(12) United States Patent
Schaller et al.

(10) Patent No.: US 9,314,252 B2
(45) Date of Patent: Apr. 19, 2016

(54) DEVICES AND METHODS FOR TREATING BONE TISSUE

(71) Applicant: Benvenue Medical, Inc., Santa Clara, CA (US)

(72) Inventors: Laurent Schaller, Los Altos, CA (US); Jeffrey L. Emery, Emerald Hills, CA (US); Timothy J. McGrath, Fremont, CA (US); James K. Lee, San Mateo, CA (US); Ryan J. Connolly, Redwood City, CA (US)

(73) Assignee: Benvenue Medical, Inc., Santa Clara, CA (US)

( * ) Notice: Subject to any disclaimer, the term of this patent is extended or adjusted under 35 U.S.C. 154(b) by 0 days.

(21) Appl. No.: 14/461,032

(22) Filed: Aug. 15, 2014

(65) Prior Publication Data
US 2014/0358145 A1  Dec. 4, 2014

Related U.S. Application Data

(63) Continuation of application No. 13/530,415, filed on Jun. 22, 2012, now Pat. No. 8,814,873.

(60) Provisional application No. 61/500,929, filed on Jun. 24, 2011.

(51) Int. Cl.
*A61B 17/16* (2006.01)
*A61B 17/70* (2006.01)
*A61B 17/00* (2006.01)

(52) U.S. Cl.
CPC .............. *A61B 17/16* (2013.01); *A61B 17/1642* (2013.01); *A61B 17/1671* (2013.01); *A61B 17/7094* (2013.01); *A61B 17/7097* (2013.01); *A61B 2017/00867* (2013.01)

(58) Field of Classification Search
CPC ...................... A61B 17/1604; A61B 17/1642
See application file for complete search history.

(56) References Cited

U.S. PATENT DOCUMENTS 1,965,653 A 7/1934 Kennedy
3,091,237 A 5/1963 Skinner
(Continued)

FOREIGN PATENT DOCUMENTS

DE 19710392 C1 7/1999
DE 202006005868 6/2006
(Continued)

OTHER PUBLICATIONS

John A. Carrino, Roxanne Chan and Alexander R. Vaccaro, "Vertebral Augmentation: Vertebroplasty and Kyphoplasty", Seminars in Roentgenology, vol. 39, No. 1 Jan. 2004: pp. 68-84.
Ajeya P. Joshi, M.D. and Paul A. Glazer, M.D., "Vertebroplasty: Current Concepts and Outlook", 2003, (9 Pages), From: http://www.spineuniverse.com/displayarticle.php/article2076.html.
PCT Invitation to Pay Additional Fees (Form PCT/ISA/206), Re: International application No. PCT/US2006/031861 dated Jan. 15, 2007.
(Continued)

*Primary Examiner* — Andrew Yang
(74) *Attorney, Agent, or Firm* — Cook Alex Ltd.

(57) ABSTRACT

The present disclosure relates to devices and methods for creating channels within bone. One method for treating bone generally includes traversing an elongated member through cancellous bone of a vertebral body along a first generally non-linear path and then retracting the elongated member, thereby leaving a generally non-linear channel. The elongated member then is traversed through the cancellous bone along a second generally non-linear path, which second path does not completely coincide with the first path and then retracted along the second generally nonlinear path, thereby leaving a second generally non-linear channel. Optionally, bone filler material is deployed into the channels.

40 Claims, 17 Drawing Sheets

(56) References Cited

U.S. PATENT DOCUMENTS

| | | |
|---|---|---|
| 3,112,743 A | 12/1963 | Cochran et al. |
| 3,648,294 A | 3/1972 | Shahrestani |
| 3,800,788 A | 4/1974 | White |
| 3,867,728 A | 2/1975 | Stubstad et al. |
| 3,875,595 A | 4/1975 | Froning |
| 3,889,665 A | 6/1975 | Ling et al. |
| 3,964,480 A | 6/1976 | Froning |
| 4,262,676 A | 4/1981 | Jamshidi |
| 4,274,163 A | 6/1981 | Malcom et al. |
| 4,312,337 A | 1/1982 | Donohue |
| 4,313,434 A | 2/1982 | Segal |
| 4,399,814 A | 8/1983 | Pratt, Jr. et al. |
| 4,462,394 A | 7/1984 | Jacobs |
| 4,466,435 A | 8/1984 | Murray |
| 4,467,479 A | 8/1984 | Brody |
| 4,488,549 A | 12/1984 | Lee et al. |
| 4,562,598 A | 1/1986 | Kranz |
| 4,595,006 A | 6/1986 | Burke et al. |
| 4,625,722 A | 12/1986 | Murray |
| 4,627,434 A | 12/1986 | Murray |
| 4,628,945 A | 12/1986 | Johnson, Jr. |
| 4,630,616 A | 12/1986 | Tretinyak |
| 4,665,906 A | 5/1987 | Jervis |
| 4,686,973 A | 8/1987 | Frisch |
| 4,697,584 A | 10/1987 | Haynes |
| 4,706,670 A | 11/1987 | Andersen et al. |
| 4,714,478 A | 12/1987 | Fischer |
| 4,743,256 A | 5/1988 | Brantigan |
| 4,772,287 A | 9/1988 | Ray et al. |
| 4,834,069 A | 5/1989 | Umeda |
| 4,838,282 A | 6/1989 | Strasser et al. |
| 4,863,476 A | 9/1989 | Shepperd |
| 4,878,915 A | 11/1989 | Brantigan |
| 4,888,022 A | 12/1989 | Huebsch |
| 4,888,024 A | 12/1989 | Powlan |
| 4,892,550 A | 1/1990 | Huebsch |
| 4,896,662 A | 1/1990 | Noble |
| 4,898,577 A | 2/1990 | Badger et al. |
| 4,904,261 A | 2/1990 | Dove et al. |
| 4,941,466 A | 7/1990 | Romano |
| 4,961,740 A | 10/1990 | Ray et al. |
| 4,969,888 A | 11/1990 | Scholten et al. |
| 5,015,247 A | 5/1991 | Michelson |
| 5,015,255 A | 5/1991 | Kuslich |
| 5,051,189 A | 9/1991 | Farrah |
| 5,053,035 A | 10/1991 | McLaren |
| 5,055,104 A | 10/1991 | Ray |
| 5,059,193 A | 10/1991 | Kuslich |
| 5,071,435 A | 12/1991 | Fuchs et al. |
| 5,098,435 A | 3/1992 | Stednitz et al. |
| 5,102,413 A | 4/1992 | Poddar |
| 5,108,404 A | 4/1992 | Scholten et al. |
| 5,122,130 A | 6/1992 | Keller |
| 5,123,926 A | 6/1992 | Pisharodi |
| 5,147,366 A | 9/1992 | Arroyo et al. |
| 5,163,989 A | 11/1992 | Campbell et al. |
| 5,171,280 A | 12/1992 | Baumgartner |
| 5,176,683 A | 1/1993 | Kimsey et al. |
| 5,176,692 A | 1/1993 | Wilk et al. |
| 5,183,052 A | 2/1993 | Terwilliger |
| 5,192,327 A | 3/1993 | Brantigan |
| 5,228,441 A | 7/1993 | Lundquist |
| 5,242,448 A | 9/1993 | Pettine et al. |
| 5,242,879 A | 9/1993 | Abe et al. |
| 5,257,632 A | 11/1993 | Turkel et al. |
| 5,263,953 A | 11/1993 | Bagby |
| 5,285,795 A | 2/1994 | Ryan et al. |
| 5,303,718 A | 4/1994 | Krajicek |
| 5,306,308 A | 4/1994 | Gross et al. |
| 5,306,310 A | 4/1994 | Siebels |
| 5,322,505 A | 6/1994 | Krause et al. |
| 5,330,429 A | 7/1994 | Noguchi et al. |
| 5,331,975 A | 7/1994 | Bonutti |
| 5,361,752 A | 11/1994 | Moll et al. |
| 5,383,932 A | 1/1995 | Wilson et al. |
| 5,385,151 A | 1/1995 | Scarfone et al. |
| 5,423,816 A | 6/1995 | Lin |
| 5,423,817 A | 6/1995 | Lin |
| 5,423,850 A | 6/1995 | Berger |
| 5,431,658 A | 7/1995 | Moskovich |
| 5,441,538 A | 8/1995 | Bonutti |
| 5,454,365 A | 10/1995 | Bonutti |
| 5,454,827 A | 10/1995 | Aust et al. |
| 5,462,563 A | 10/1995 | Shearer et al. |
| 5,468,245 A | 11/1995 | Vargas, III |
| 5,480,400 A | 1/1996 | Berger |
| 5,484,437 A | 1/1996 | Michelson |
| 5,509,923 A | 4/1996 | Middleman et al. |
| 5,514,143 A | 5/1996 | Bonutti et al. |
| 5,514,153 A | 5/1996 | Bonutti |
| 5,522,398 A | 6/1996 | Goldenberg et al. |
| 5,522,790 A | 6/1996 | Moll et al. |
| 5,522,846 A | 6/1996 | Bonutti |
| 5,527,343 A | 6/1996 | Bonutti |
| 5,527,624 A | 6/1996 | Higgins et al. |
| 5,531,856 A | 7/1996 | Moll et al. |
| 5,534,023 A | 7/1996 | Henley |
| 5,538,009 A | 7/1996 | Byrne et al. |
| 5,540,711 A | 7/1996 | Kieturakis et al. |
| 5,545,222 A | 8/1996 | Bonutti |
| 5,549,679 A | 8/1996 | Kuslich |
| 5,562,736 A | 10/1996 | Ray et al. |
| 5,571,109 A | 11/1996 | Bertagnoli |
| 5,571,189 A | 11/1996 | Kuslich |
| 5,571,190 A | 11/1996 | Ulrich et al. |
| 5,575,790 A | 11/1996 | Chen et al. |
| 5,593,409 A | 1/1997 | Michelson |
| 5,601,556 A | 2/1997 | Pisharodi |
| 5,601,572 A | 2/1997 | Middleman et al. |
| 5,632,746 A | 5/1997 | Middleman et al. |
| 5,645,597 A | 7/1997 | Krapiva |
| 5,665,122 A | 9/1997 | Kambin |
| 5,669,926 A | 9/1997 | Aust |
| 5,674,295 A | 10/1997 | Ray et al. |
| 5,681,263 A | 10/1997 | Flesch |
| 5,693,100 A | 12/1997 | Pisharodi |
| 5,695,513 A | 12/1997 | Johnson |
| 5,702,453 A | 12/1997 | Rabbe et al. |
| 5,702,454 A | 12/1997 | Baumgartner |
| 5,716,416 A | 2/1998 | Lin |
| 5,741,253 A | 4/1998 | Michelson |
| 5,749,879 A | 5/1998 | Middleman et al. |
| 5,755,797 A | 5/1998 | Baumgartner |
| 5,756,127 A | 5/1998 | Grisoni et al. |
| 5,772,661 A | 6/1998 | Michelson |
| 5,782,832 A | 7/1998 | Larsen et al. |
| 5,788,703 A | 8/1998 | Mittelmeier et al. |
| 5,807,275 A | 9/1998 | Jamshidi |
| 5,820,628 A | 10/1998 | Middleman et al. |
| 5,824,093 A | 10/1998 | Ray et al. |
| 5,827,289 A | 10/1998 | Reiley et al. |
| 5,836,948 A | 11/1998 | Zucherman et al. |
| 5,848,986 A | 12/1998 | Lundquist et al. |
| 5,860,977 A | 1/1999 | Zucherman et al. |
| 5,865,848 A | 2/1999 | Baker |
| 5,871,470 A | 2/1999 | McWha |
| 5,904,690 A | 5/1999 | Middleman et al. |
| 5,919,235 A | 7/1999 | Husson et al. |
| 5,925,074 A | 7/1999 | Gingras et al. |
| 5,961,554 A | 10/1999 | Janson et al. |
| 5,972,015 A | 10/1999 | Scribner et al. |
| 5,976,186 A | 11/1999 | Bao et al. |
| 5,980,522 A | 11/1999 | Koros et al. |
| 6,012,494 A | 1/2000 | Balazs |
| 6,015,436 A | 1/2000 | Schonhoffer |
| 6,019,793 A | 2/2000 | Perren et al. |
| 6,030,401 A | 2/2000 | Marino |
| 6,033,406 A | 3/2000 | Mathews |
| 6,033,412 A | 3/2000 | Losken et al. |
| 6,039,740 A | 3/2000 | Olerud |
| 6,045,552 A | 4/2000 | Zucherman et al. |
| 6,048,342 A | 4/2000 | Zucherman et al. |
| 6,048,346 A | 4/2000 | Reiley et al. |
| 6,048,360 A | 4/2000 | Khosravi et al. |

(56) References Cited

U.S. PATENT DOCUMENTS

| | | |
|---|---|---|
| 6,066,154 A | 5/2000 | Reiley et al. |
| 6,068,630 A | 5/2000 | Zucherman et al. |
| 6,073,051 A | 6/2000 | Sharkey et al. |
| 6,083,225 A | 7/2000 | Winslow et al. |
| 6,090,143 A | 7/2000 | Meriwether et al. |
| 6,102,950 A | 8/2000 | Vaccaro |
| 6,110,210 A | 8/2000 | Norton et al. |
| 6,113,640 A | 9/2000 | Tormala et al. |
| 6,119,044 A | 9/2000 | Kuzma |
| 6,123,705 A | 9/2000 | Michelson |
| 6,126,660 A | 10/2000 | Dietz |
| 6,127,597 A | 10/2000 | Beyar et al. |
| 6,159,211 A | 12/2000 | Boriani et al. |
| 6,159,244 A | 12/2000 | Suddaby |
| 6,165,218 A | 12/2000 | Husson et al. |
| 6,174,337 B1 | 1/2001 | Keenan |
| 6,179,873 B1 | 1/2001 | Zientek |
| 6,187,048 B1 | 2/2001 | Milner et al. |
| 6,190,414 B1 | 2/2001 | Young et al. |
| 6,193,757 B1 | 2/2001 | Foley et al. |
| 6,197,033 B1 | 3/2001 | Haid, Jr. et al. |
| D439,980 S | 4/2001 | Reiley et al. |
| 6,217,579 B1 | 4/2001 | Koros |
| 6,221,082 B1 | 4/2001 | Marino et al. |
| 6,224,603 B1 | 5/2001 | Marino |
| 6,235,030 B1 | 5/2001 | Zucherman et al. |
| 6,235,043 B1 | 5/2001 | Reiley et al. |
| 6,238,491 B1 | 5/2001 | Davidson et al. |
| 6,241,734 B1 | 6/2001 | Scribner et al. |
| 6,248,110 B1 | 6/2001 | Reiley et al. |
| 6,251,140 B1 | 6/2001 | Marino et al. |
| 6,261,289 B1 | 7/2001 | Levy |
| 6,264,695 B1 | 7/2001 | Stoy |
| 6,267,763 B1 | 7/2001 | Castro |
| 6,280,456 B1 | 8/2001 | Scribner et al. |
| 6,280,475 B1 | 8/2001 | Bao et al. |
| 6,290,724 B1 | 9/2001 | Marino |
| D449,691 S | 10/2001 | Reiley et al. |
| 6,296,647 B1 | 10/2001 | Robioneck et al. |
| 6,312,443 B1 | 11/2001 | Stone |
| 6,364,828 B1 | 4/2002 | Yeung et al. |
| 6,368,325 B1 | 4/2002 | McKinley et al. |
| 6,387,130 B1 | 5/2002 | Stone et al. |
| 6,402,750 B1 | 6/2002 | Atkinson et al. |
| 6,419,641 B1 | 7/2002 | Mark et al. |
| 6,419,705 B1 | 7/2002 | Erickson |
| 6,423,071 B1 | 7/2002 | Lawson |
| 6,423,083 B2 | 7/2002 | Reiley et al. |
| 6,423,089 B1 | 7/2002 | Gingras et al. |
| 6,425,887 B1 | 7/2002 | McGuckin et al. |
| 6,425,919 B1 | 7/2002 | Lambrecht |
| 6,428,541 B1 | 8/2002 | Boyd et al. |
| 6,436,140 B1 | 8/2002 | Liu et al. |
| 6,440,138 B1 | 8/2002 | Reiley et al. |
| 6,451,019 B1 | 9/2002 | Zucherman et al. |
| 6,468,279 B1 | 10/2002 | Reo |
| 6,478,805 B1 | 11/2002 | Marino et al. |
| 6,482,235 B1 | 11/2002 | Lambrecht et al. |
| 6,485,518 B1 | 11/2002 | Cornwall et al. |
| D467,657 S | 12/2002 | Scribner |
| 6,488,710 B2 | 12/2002 | Besselink |
| 6,491,626 B1 | 12/2002 | Stone et al. |
| 6,491,695 B1 | 12/2002 | Roggenbuck |
| 6,498,421 B1 | 12/2002 | Oh et al. |
| 6,500,178 B2 | 12/2002 | Zucherman et al. |
| 6,500,205 B1 | 12/2002 | Michelson |
| 6,508,839 B1 | 1/2003 | Lambrecht et al. |
| 6,511,471 B2 | 1/2003 | Rosenman et al. |
| 6,512,958 B1 | 1/2003 | Swoyer et al. |
| D469,871 S | 2/2003 | Sand |
| 6,520,991 B2 | 2/2003 | Huene |
| D472,323 S | 3/2003 | Sand |
| 6,530,930 B1 | 3/2003 | Marino et al. |
| 6,533,791 B1 | 3/2003 | Betz et al. |
| 6,533,797 B1 | 3/2003 | Stone et al. |
| 6,540,747 B1 | 4/2003 | Marino |
| 6,554,833 B2 | 4/2003 | Levy et al. |
| 6,558,390 B2 | 5/2003 | Cragg |
| 6,562,074 B2 | 5/2003 | Gerbec et al. |
| 6,572,593 B1 | 6/2003 | Daum |
| 6,575,919 B1 | 6/2003 | Reiley et al. |
| 6,575,979 B1 | 6/2003 | Cragg |
| 6,576,016 B1 | 6/2003 | Hochshuler et al. |
| 6,579,291 B1 | 6/2003 | Keith et al. |
| 6,582,431 B1 | 6/2003 | Ray |
| 6,582,433 B2 | 6/2003 | Yun |
| 6,592,559 B1 | 7/2003 | Pakter et al. |
| 6,595,998 B2 | 7/2003 | Johnson et al. |
| 6,602,293 B1 | 8/2003 | Biermann et al. |
| 6,607,530 B1 | 8/2003 | Carl et al. |
| 6,607,544 B1 | 8/2003 | Boucher et al. |
| 6,610,094 B2 | 8/2003 | Husson |
| 6,613,054 B2 | 9/2003 | Scribner et al. |
| 6,620,196 B1 | 9/2003 | Trieu |
| 6,623,505 B2 | 9/2003 | Scribner et al. |
| D482,787 S | 11/2003 | Reiss |
| 6,641,587 B2 | 11/2003 | Scribner et al. |
| 6,645,213 B2 | 11/2003 | Sand et al. |
| 6,648,917 B2 | 11/2003 | Gerbec et al. |
| D483,495 S | 12/2003 | Sand |
| 6,656,178 B1 | 12/2003 | Veldhuizen et al. |
| 6,656,180 B2 | 12/2003 | Stahurski |
| 6,660,037 B1 | 12/2003 | Husson et al. |
| 6,663,647 B2 | 12/2003 | Reiley et al. |
| 6,666,890 B2 | 12/2003 | Michelson |
| 6,666,891 B2 | 12/2003 | Boehm, Jr. et al. |
| 6,676,663 B2 | 1/2004 | Higueras et al. |
| 6,676,665 B2 | 1/2004 | Foley et al. |
| 6,682,561 B2 | 1/2004 | Songer et al. |
| 6,685,742 B1 | 2/2004 | Jackson |
| 6,689,125 B1 | 2/2004 | Keith et al. |
| 6,689,168 B2 | 2/2004 | Lieberman |
| 6,692,563 B2 | 2/2004 | Zimmermann |
| 6,706,070 B1 | 3/2004 | Wagner et al. |
| 6,716,216 B1 | 4/2004 | Boucher et al. |
| 6,716,247 B2 | 4/2004 | Michelson |
| 6,716,957 B2 | 4/2004 | Tunc |
| 6,719,761 B1 | 4/2004 | Reiley et al. |
| 6,719,773 B1 | 4/2004 | Boucher et al. |
| 6,723,128 B2 | 4/2004 | Uk |
| 6,726,691 B2 | 4/2004 | Osorio et al. |
| D490,159 S | 5/2004 | Sand |
| 6,740,093 B2 | 5/2004 | Hochschuler et al. |
| D492,032 S | 6/2004 | Muller et al. |
| 6,749,560 B1 | 6/2004 | Konstorum et al. |
| 6,755,841 B2 | 6/2004 | Fraser et al. |
| D492,775 S | 7/2004 | Doelling et al. |
| D493,533 S | 7/2004 | Blain |
| 6,758,673 B2 | 7/2004 | Fromovich et al. |
| 6,764,514 B1 | 7/2004 | Li et al. |
| D495,417 S | 8/2004 | Doelling et al. |
| 6,773,460 B2 | 8/2004 | Jackson |
| 6,780,151 B2 | 8/2004 | Grabover et al. |
| 6,783,530 B1 | 8/2004 | Levy |
| 6,793,679 B2 | 9/2004 | Michelson |
| 6,796,983 B1 | 9/2004 | Zucherman et al. |
| 6,805,695 B2 | 10/2004 | Keith et al. |
| 6,805,697 B1 | 10/2004 | Helm et al. |
| 6,808,537 B2 | 10/2004 | Michelson |
| 6,814,736 B2 | 11/2004 | Reiley et al. |
| 6,814,756 B1 | 11/2004 | Michelson |
| 6,821,298 B1 | 11/2004 | Jackson |
| 6,830,589 B2 | 12/2004 | Erickson |
| 6,835,205 B2 | 12/2004 | Atkinson et al. |
| 6,835,206 B2 | 12/2004 | Jackson |
| 6,840,944 B2 | 1/2005 | Suddaby |
| 6,852,126 B2 | 2/2005 | Ahlgren |
| 6,852,129 B2 | 2/2005 | Gerbec et al. |
| 6,863,668 B2 | 3/2005 | Gillespie et al. |
| 6,863,672 B2 | 3/2005 | Reiley et al. |
| 6,863,673 B2 | 3/2005 | Gerbec et al. |
| 6,866,682 B1 | 3/2005 | An et al. |
| 6,875,219 B2 | 4/2005 | Arramon et al. |
| 6,881,228 B2 | 4/2005 | Zdeblick et al. |

(56) References Cited

U.S. PATENT DOCUMENTS

| | | |
|---|---|---|
| 6,883,520 B2 | 4/2005 | Lambrecht et al. |
| 6,887,248 B2 | 5/2005 | McKinley et al. |
| 6,893,466 B2 | 5/2005 | Trieu |
| 6,899,716 B2 | 5/2005 | Cragg |
| 6,899,719 B2 | 5/2005 | Reiley et al. |
| D506,828 S | 6/2005 | Layne et al. |
| 6,905,512 B2 | 6/2005 | Paes et al. |
| 6,908,506 B2 | 6/2005 | Zimmermann |
| 6,921,403 B2 | 7/2005 | Cragg et al. |
| 6,923,810 B1 | 8/2005 | Michelson |
| 6,923,813 B2 | 8/2005 | Phillips et al. |
| 6,923,814 B1 | 8/2005 | Hildebrand et al. |
| 6,929,647 B2 | 8/2005 | Cohen |
| 6,945,973 B2 | 9/2005 | Bray |
| 6,952,129 B2 | 10/2005 | Lin et al. |
| 6,962,606 B2 | 11/2005 | Michelson |
| 6,964,674 B1 | 11/2005 | Matsuura et al. |
| D512,506 S | 12/2005 | Layne et al. |
| 6,972,035 B2 | 12/2005 | Michelson |
| 6,974,479 B2 | 12/2005 | Trieu |
| 6,979,341 B2 | 12/2005 | Scribner et al. |
| 6,981,981 B2 | 1/2006 | Reiley et al. |
| 6,997,929 B2 | 2/2006 | Manzi et al. |
| 7,004,945 B2 | 2/2006 | Boyd et al. |
| 7,008,453 B1 | 3/2006 | Michelson |
| 7,014,633 B2 | 3/2006 | Cragg |
| 7,018,089 B2 | 3/2006 | Wenz et al. |
| 7,018,415 B1 | 3/2006 | McKay |
| 7,018,453 B2 | 3/2006 | Klein et al. |
| 7,029,498 B2 | 4/2006 | Boehm et al. |
| 7,044,954 B2 | 5/2006 | Reiley et al. |
| 7,048,694 B2 | 5/2006 | Mark et al. |
| 7,063,703 B2 | 6/2006 | Reo |
| 7,066,961 B2 | 6/2006 | Michelson |
| 7,069,087 B2 | 6/2006 | Sharkey et al. |
| 7,070,598 B2 | 7/2006 | Lim et al. |
| 7,074,226 B2 | 7/2006 | Roehm, III et al. |
| 7,081,120 B2 | 7/2006 | Li et al. |
| 7,081,122 B1 | 7/2006 | Reiley et al. |
| 7,087,055 B2 | 8/2006 | Lim et al. |
| 7,094,257 B2 | 8/2006 | Mujwid et al. |
| 7,115,128 B2 | 10/2006 | Michelson |
| 7,115,163 B2 | 10/2006 | Zimmermann |
| 7,118,579 B2 | 10/2006 | Michelson |
| 7,118,580 B1 | 10/2006 | Beyersdorff et al. |
| 7,118,598 B2 | 10/2006 | Michelson |
| 7,124,761 B2 | 10/2006 | Lambrecht et al. |
| 7,128,760 B2 | 10/2006 | Michelson |
| 7,135,424 B2 | 11/2006 | Worley et al. |
| 7,153,304 B2 | 12/2006 | Robie et al. |
| 7,153,305 B2 | 12/2006 | Johnson et al. |
| 7,153,306 B2 | 12/2006 | Ralph et al. |
| 7,153,307 B2 | 12/2006 | Scribner et al. |
| 7,156,874 B2 | 1/2007 | Paponneau et al. |
| 7,156,875 B2 | 1/2007 | Michelson |
| 7,166,107 B2 | 1/2007 | Anderson |
| 7,179,293 B2 | 2/2007 | McKay |
| 7,189,242 B2 | 3/2007 | Boyd et al. |
| 7,204,851 B2 | 4/2007 | Trieu et al. |
| 7,207,991 B2 | 4/2007 | Michelson |
| 7,211,112 B2 | 5/2007 | Baynham et al. |
| 7,214,227 B2 | 5/2007 | Colleran et al. |
| 7,220,281 B2 | 5/2007 | Lambrecht et al. |
| 7,223,227 B2 | 5/2007 | Pflueger |
| 7,226,481 B2 | 6/2007 | Kuslich |
| 7,241,297 B2 | 7/2007 | Shaolian et al. |
| 7,244,273 B2 | 7/2007 | Pedersen et al. |
| 7,250,060 B2 | 7/2007 | Trieu |
| 7,252,671 B2 | 8/2007 | Scribner et al. |
| 7,267,687 B2 | 9/2007 | McGuckin, Jr. |
| 7,270,679 B2 | 9/2007 | Istephanous et al. |
| 7,276,062 B2 | 10/2007 | McDaniel et al. |
| 7,311,713 B2 | 12/2007 | Johnson et al. |
| 7,318,840 B2 | 1/2008 | McKay |
| 7,320,689 B2 | 1/2008 | Keller |
| 7,322,962 B2 | 1/2008 | Forrest |
| 7,608,083 B2 | 10/2009 | Lee et al. |
| 7,637,905 B2 | 12/2009 | Saadat et al. |
| 7,713,273 B2 | 5/2010 | Krueger et al. |
| 7,799,035 B2 | 9/2010 | Krueger et al. |
| 7,828,807 B2 | 11/2010 | LeHuec et al. |
| 8,057,544 B2 | 11/2011 | Schaller |
| 8,128,633 B2 | 3/2012 | Linderman et al. |
| 8,187,327 B2 | 5/2012 | Edidin et al. |
| 8,236,029 B2 | 8/2012 | Siegal |
| D669,168 S | 10/2012 | Krueger et al. |
| 8,529,576 B2 | 9/2013 | Krueger et al. |
| 2001/0011174 A1 | 8/2001 | Reiley et al. |
| 2001/0016741 A1 | 8/2001 | Burkus et al. |
| 2002/0016583 A1 | 2/2002 | Cragg |
| 2002/0026195 A1 | 2/2002 | Layne et al. |
| 2002/0026244 A1 | 2/2002 | Trieu |
| 2002/0068974 A1 | 6/2002 | Kuslich et al. |
| 2002/0077700 A1 | 6/2002 | Varga et al. |
| 2002/0082584 A1 | 6/2002 | Rosenman et al. |
| 2002/0082608 A1 | 6/2002 | Reiley et al. |
| 2002/0087163 A1 | 7/2002 | Dixon et al. |
| 2002/0091390 A1 | 7/2002 | Michelson |
| 2002/0099385 A1 | 7/2002 | Ralph et al. |
| 2002/0107519 A1 | 8/2002 | Dixon et al. |
| 2002/0156482 A1 | 10/2002 | Scribner et al. |
| 2002/0169471 A1 | 11/2002 | Ferdinand |
| 2002/0172851 A1 | 11/2002 | Corey et al. |
| 2002/0173796 A1 | 11/2002 | Cragg |
| 2002/0173841 A1 | 11/2002 | Ortiz et al. |
| 2002/0173851 A1 | 11/2002 | McKay |
| 2002/0183761 A1 | 12/2002 | Johnson et al. |
| 2002/0183778 A1 | 12/2002 | Reiley et al. |
| 2002/0191487 A1 | 12/2002 | Sand |
| 2003/0018390 A1 | 1/2003 | Husson |
| 2003/0032963 A1 | 2/2003 | Reiss et al. |
| 2003/0050644 A1 | 3/2003 | Boucher et al. |
| 2003/0069593 A1 | 4/2003 | Tremulis et al. |
| 2003/0074075 A1 | 4/2003 | Thomas, Jr. et al. |
| 2003/0108588 A1 | 6/2003 | Chen et al. |
| 2003/0130664 A1 | 7/2003 | Boucher et al. |
| 2003/0171812 A1 | 9/2003 | Grunberg et al. |
| 2003/0191414 A1 | 10/2003 | Reiley et al. |
| 2003/0191489 A1 | 10/2003 | Reiley et al. |
| 2003/0195518 A1 | 10/2003 | Cragg |
| 2003/0195547 A1 | 10/2003 | Scribner et al. |
| 2003/0195630 A1 | 10/2003 | Ferree |
| 2003/0199979 A1 | 10/2003 | McGuckin, Jr. |
| 2003/0208136 A1 | 11/2003 | Mark et al. |
| 2003/0220648 A1 | 11/2003 | Osorio et al. |
| 2003/0220695 A1 | 11/2003 | Sevrain |
| 2003/0229372 A1 | 12/2003 | Reiley et al. |
| 2003/0233096 A1 | 12/2003 | Osorio et al. |
| 2004/0010251 A1 | 1/2004 | Pitaru et al. |
| 2004/0010260 A1 | 1/2004 | Scribner et al. |
| 2004/0010263 A1 | 1/2004 | Boucher et al. |
| 2004/0019354 A1 | 1/2004 | Johnson et al. |
| 2004/0024408 A1 | 2/2004 | Burkus et al. |
| 2004/0024409 A1 | 2/2004 | Sand et al. |
| 2004/0024463 A1 | 2/2004 | Thomas, Jr. et al. |
| 2004/0024465 A1 | 2/2004 | Lambrecht et al. |
| 2004/0034343 A1 | 2/2004 | Gillespie et al. |
| 2004/0034429 A1 | 2/2004 | Lambrecht et al. |
| 2004/0049203 A1 | 3/2004 | Scribner et al. |
| 2004/0059339 A1 | 3/2004 | Roehm, III et al. |
| 2004/0059418 A1 | 3/2004 | McKay et al. |
| 2004/0064144 A1 | 4/2004 | Johnson et al. |
| 2004/0073308 A1 | 4/2004 | Kuslich et al. |
| 2004/0082953 A1 | 4/2004 | Petit |
| 2004/0087947 A1 | 5/2004 | Lim et al. |
| 2004/0092933 A1 | 5/2004 | Shaolian et al. |
| 2004/0092948 A1 | 5/2004 | Stevens et al. |
| 2004/0092988 A1 | 5/2004 | Shaolian et al. |
| 2004/0097924 A1 | 5/2004 | Lambrecht et al. |
| 2004/0097930 A1 | 5/2004 | Justis et al. |
| 2004/0097932 A1 | 5/2004 | Ray, III et al. |
| 2004/0102774 A1 | 5/2004 | Trieu |
| 2004/0106940 A1 | 6/2004 | Shaolian et al. |
| 2004/0111161 A1 | 6/2004 | Trieu |

(56) References Cited

U.S. PATENT DOCUMENTS

| | | |
|---|---|---|
| 2004/0117019 A1 | 6/2004 | Trieu et al. |
| 2004/0133124 A1 | 7/2004 | Bates et al. |
| 2004/0133229 A1 | 7/2004 | Lambrecht et al. |
| 2004/0133280 A1 | 7/2004 | Trieu |
| 2004/0138748 A1 | 7/2004 | Boyer, II et al. |
| 2004/0153064 A1 | 8/2004 | Foley et al. |
| 2004/0153115 A1 | 8/2004 | Reiley et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0176775 A1 | 9/2004 | Burkus et al. |
| 2004/0186471 A1 | 9/2004 | Trieu |
| 2004/0186528 A1 | 9/2004 | Ries et al. |
| 2004/0186573 A1 | 9/2004 | Ferree |
| 2004/0210231 A1 | 10/2004 | Boucher et al. |
| 2004/0210310 A1 | 10/2004 | Trieu |
| 2004/0215344 A1 | 10/2004 | Hochschuler et al. |
| 2004/0220580 A1 | 11/2004 | Johnson et al. |
| 2004/0220672 A1 | 11/2004 | Shadduck |
| 2004/0225296 A1 | 11/2004 | Reiss et al. |
| 2004/0225361 A1 | 11/2004 | Glenn et al. |
| 2004/0230191 A1 | 11/2004 | Frey et al. |
| 2004/0230309 A1 | 11/2004 | DiMauro et al. |
| 2004/0243229 A1 | 12/2004 | Vidlund et al. |
| 2004/0249377 A1 | 12/2004 | Kaes et al. |
| 2004/0254520 A1 | 12/2004 | Porteous et al. |
| 2004/0254644 A1 | 12/2004 | Taylor |
| 2004/0260300 A1 | 12/2004 | Gorensek et al. |
| 2004/0260397 A1 | 12/2004 | Lambrecht et al. |
| 2004/0267271 A9 | 12/2004 | Scribner et al. |
| 2005/0004578 A1 | 1/2005 | Lambrecht et al. |
| 2005/0010293 A1 | 1/2005 | Zucherman et al. |
| 2005/0010298 A1 | 1/2005 | Zucherman et al. |
| 2005/0015148 A1 | 1/2005 | Jansen et al. |
| 2005/0015152 A1 | 1/2005 | Sweeney |
| 2005/0033295 A1 | 2/2005 | Wisnewski |
| 2005/0033440 A1 | 2/2005 | Lambrecht et al. |
| 2005/0038517 A1 | 2/2005 | Carrison et al. |
| 2005/0043737 A1 | 2/2005 | Reiley et al. |
| 2005/0043796 A1 | 2/2005 | Grant et al. |
| 2005/0054948 A1 | 3/2005 | Goldenberg |
| 2005/0055097 A1 | 3/2005 | Grunberg et al. |
| 2005/0060036 A1 | 3/2005 | Schultz et al. |
| 2005/0060038 A1 | 3/2005 | Lambrecht et al. |
| 2005/0065519 A1 | 3/2005 | Michelson |
| 2005/0065609 A1 | 3/2005 | Wardlaw |
| 2005/0069571 A1 | 3/2005 | Slivka et al. |
| 2005/0070908 A1 | 3/2005 | Cragg |
| 2005/0070911 A1 | 3/2005 | Carrison et al. |
| 2005/0070913 A1 | 3/2005 | Milbocker et al. |
| 2005/0071011 A1 | 3/2005 | Ralph et al. |
| 2005/0080488 A1 | 4/2005 | Schultz |
| 2005/0085912 A1 | 4/2005 | Arnin et al. |
| 2005/0090833 A1 | 4/2005 | DiPoto |
| 2005/0090852 A1 | 4/2005 | Layne et al. |
| 2005/0090899 A1 | 4/2005 | DiPoto |
| 2005/0107880 A1 | 5/2005 | Shimp et al. |
| 2005/0113918 A1 | 5/2005 | Messerli et al. |
| 2005/0113919 A1 | 5/2005 | Cragg et al. |
| 2005/0113928 A1 | 5/2005 | Cragg et al. |
| 2005/0118228 A1 | 6/2005 | Trieu |
| 2005/0119662 A1 | 6/2005 | Reiley et al. |
| 2005/0119750 A1 | 6/2005 | Studer |
| 2005/0119751 A1 | 6/2005 | Lawson |
| 2005/0119752 A1 | 6/2005 | Williams et al. |
| 2005/0119754 A1 | 6/2005 | Trieu et al. |
| 2005/0124989 A1 | 6/2005 | Suddaby |
| 2005/0124992 A1 | 6/2005 | Ferree |
| 2005/0124999 A1 | 6/2005 | Teitelbaum et al. |
| 2005/0125066 A1 | 6/2005 | McAfee |
| 2005/0131267 A1 | 6/2005 | Talmadge |
| 2005/0131268 A1 | 6/2005 | Talmadge |
| 2005/0131269 A1 | 6/2005 | Talmadge |
| 2005/0131536 A1 | 6/2005 | Eisermann et al. |
| 2005/0131540 A1 | 6/2005 | Trieu |
| 2005/0131541 A1 | 6/2005 | Trieu |
| 2005/0137602 A1 | 6/2005 | Assell et al. |
| 2005/0142211 A1 | 6/2005 | Wenz |
| 2005/0143763 A1 | 6/2005 | Ortiz et al. |
| 2005/0143827 A1 | 6/2005 | Globerman et al. |
| 2005/0149022 A1 | 7/2005 | Shaolian et al. |
| 2005/0149191 A1 | 7/2005 | Cragg et al. |
| 2005/0149194 A1 | 7/2005 | Ahlgren |
| 2005/0149197 A1 | 7/2005 | Cauthen |
| 2005/0154396 A1 | 7/2005 | Foley et al. |
| 2005/0154463 A1 | 7/2005 | Trieu |
| 2005/0165406 A1 | 7/2005 | Assell et al. |
| 2005/0171539 A1 | 8/2005 | Braun et al. |
| 2005/0171552 A1 | 8/2005 | Johnson et al. |
| 2005/0182412 A1 | 8/2005 | Johnson et al. |
| 2005/0182413 A1 | 8/2005 | Johnson et al. |
| 2005/0182414 A1 | 8/2005 | Manzi et al. |
| 2005/0187556 A1 | 8/2005 | Stack et al. |
| 2005/0187558 A1 | 8/2005 | Johnson et al. |
| 2005/0187559 A1 | 8/2005 | Raymond et al. |
| 2005/0187564 A1 | 8/2005 | Jayaraman |
| 2005/0197707 A1 | 9/2005 | Trieu et al. |
| 2005/0216018 A1 | 9/2005 | Sennett |
| 2005/0216087 A1 | 9/2005 | Zucherman et al. |
| 2005/0222684 A1 | 10/2005 | Ferree |
| 2005/0228383 A1 | 10/2005 | Zucherman et al. |
| 2005/0228391 A1 | 10/2005 | Levy et al. |
| 2005/0228397 A1 | 10/2005 | Malandain et al. |
| 2005/0234425 A1 | 10/2005 | Miller et al. |
| 2005/0234451 A1 | 10/2005 | Markworth |
| 2005/0234452 A1 | 10/2005 | Malandain |
| 2005/0234456 A1 | 10/2005 | Malandain |
| 2005/0240182 A1 | 10/2005 | Zucherman et al. |
| 2005/0240189 A1 | 10/2005 | Rousseau et al. |
| 2005/0240193 A1 | 10/2005 | Layne et al. |
| 2005/0240269 A1 | 10/2005 | Lambrecht et al. |
| 2005/0251149 A1 | 11/2005 | Wenz |
| 2005/0251260 A1 | 11/2005 | Gerber et al. |
| 2005/0261684 A1 | 11/2005 | Shaolian et al. |
| 2005/0261695 A1 | 11/2005 | Cragg et al. |
| 2005/0261781 A1 | 11/2005 | Sennett et al. |
| 2005/0273166 A1 | 12/2005 | Sweeney |
| 2005/0278023 A1 | 12/2005 | Zwirkoski |
| 2005/0278027 A1 | 12/2005 | Hyde, Jr. |
| 2005/0278029 A1 | 12/2005 | Trieu |
| 2005/0283244 A1 | 12/2005 | Gordon et al. |
| 2005/0287071 A1 | 12/2005 | Wenz |
| 2006/0004456 A1 | 1/2006 | McKay |
| 2006/0009779 A1 | 1/2006 | Collins et al. |
| 2006/0030850 A1 | 2/2006 | Keegan et al. |
| 2006/0030943 A1 | 2/2006 | Peterman |
| 2006/0036259 A1 | 2/2006 | Carl et al. |
| 2006/0064171 A1 | 3/2006 | Trieu |
| 2006/0069439 A1 | 3/2006 | Zucherman et al. |
| 2006/0069440 A1 | 3/2006 | Zucherman et al. |
| 2006/0085002 A1 | 4/2006 | Trieu et al. |
| 2006/0085009 A1 | 4/2006 | Truckai et al. |
| 2006/0089642 A1 | 4/2006 | Diaz et al. |
| 2006/0089646 A1 | 4/2006 | Bonutti |
| 2006/0089654 A1 | 4/2006 | Lins et al. |
| 2006/0089715 A1 | 4/2006 | Truckai et al. |
| 2006/0089718 A1 | 4/2006 | Zucherman et al. |
| 2006/0089719 A1 | 4/2006 | Trieu |
| 2006/0095045 A1 | 5/2006 | Trieu |
| 2006/0095046 A1 | 5/2006 | Trieu et al. |
| 2006/0095134 A1 | 5/2006 | Trieu et al. |
| 2006/0095138 A1 | 5/2006 | Truckai et al. |
| 2006/0100706 A1 | 5/2006 | Shadduck et al. |
| 2006/0106397 A1 | 5/2006 | Lins |
| 2006/0106459 A1 | 5/2006 | Truckai et al. |
| 2006/0122704 A1 | 6/2006 | Vresilovic et al. |
| 2006/0136064 A1 | 6/2006 | Sherman |
| 2006/0142858 A1 | 6/2006 | Colleran et al. |
| 2006/0142864 A1 | 6/2006 | Cauthen |
| 2006/0149136 A1 | 7/2006 | Seto et al. |
| 2006/0149237 A1 | 7/2006 | Markworth et al. |
| 2006/0149252 A1 | 7/2006 | Markworth et al. |
| 2006/0149268 A1 | 7/2006 | Truckai et al. |
| 2006/0149380 A1 | 7/2006 | Lotz et al. |

(56) References Cited

U.S. PATENT DOCUMENTS

| | | |
|---|---|---|
| 2006/0149397 A1 | 7/2006 | Giehrl et al. |
| 2006/0155379 A1 | 7/2006 | Heneveld, Sr. et al. |
| 2006/0161162 A1 | 7/2006 | Lambrecht et al. |
| 2006/0161166 A1 | 7/2006 | Johnson et al. |
| 2006/0167553 A1 | 7/2006 | Cauthen, III et al. |
| 2006/0173545 A1 | 8/2006 | Cauthen, III et al. |
| 2006/0178746 A1 | 8/2006 | Bartish, Jr. et al. |
| 2006/0184192 A1 | 8/2006 | Markworth et al. |
| 2006/0184247 A1 | 8/2006 | Edidin et al. |
| 2006/0184248 A1 | 8/2006 | Edidin et al. |
| 2006/0189999 A1 | 8/2006 | Zwirkoski |
| 2006/0190083 A1 | 8/2006 | Arnin et al. |
| 2006/0190085 A1 | 8/2006 | Cauthen |
| 2006/0195102 A1 | 8/2006 | Malandain |
| 2006/0200139 A1 | 9/2006 | Michelson |
| 2006/0200164 A1 | 9/2006 | Michelson |
| 2006/0200239 A1 | 9/2006 | Rothman et al. |
| 2006/0200240 A1 | 9/2006 | Rothman et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206116 A1 | 9/2006 | Yeung |
| 2006/0206207 A1 | 9/2006 | Dryer et al. |
| 2006/0235423 A1 | 10/2006 | Cantu |
| 2006/0235521 A1 | 10/2006 | Zucherman et al. |
| 2006/0241770 A1 | 10/2006 | Rhoda et al. |
| 2006/0247770 A1 | 11/2006 | Peterman |
| 2006/0247771 A1 | 11/2006 | Peterman et al. |
| 2006/0247781 A1 | 11/2006 | Francis |
| 2006/0264896 A1 | 11/2006 | Palmer |
| 2006/0264939 A1 | 11/2006 | Zucherman et al. |
| 2006/0264945 A1 | 11/2006 | Edidin et al. |
| 2006/0265067 A1 | 11/2006 | Zucherman et al. |
| 2006/0265077 A1 | 11/2006 | Zwirkoski |
| 2006/0271049 A1 | 11/2006 | Zucherman et al. |
| 2006/0271061 A1 | 11/2006 | Beyar et al. |
| 2006/0276899 A1 | 12/2006 | Zipnick et al. |
| 2006/0282167 A1 | 12/2006 | Lambrecht et al. |
| 2006/0287726 A1 | 12/2006 | Segal et al. |
| 2006/0293662 A1 | 12/2006 | Boyer, II et al. |
| 2006/0293753 A1 | 12/2006 | Thramann |
| 2007/0006692 A1 | 1/2007 | Phan |
| 2007/0010716 A1 | 1/2007 | Malandain et al. |
| 2007/0010717 A1 | 1/2007 | Cragg |
| 2007/0010824 A1 | 1/2007 | Malandain et al. |
| 2007/0010844 A1 | 1/2007 | Gong et al. |
| 2007/0010845 A1 | 1/2007 | Gong et al. |
| 2007/0010846 A1 | 1/2007 | Leung et al. |
| 2007/0010848 A1 | 1/2007 | Leung et al. |
| 2007/0010889 A1 | 1/2007 | Francis |
| 2007/0032703 A1 | 2/2007 | Sankaran et al. |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0048382 A1 | 3/2007 | Meyer et al. |
| 2007/0049849 A1 | 3/2007 | Schwardt et al. |
| 2007/0049934 A1 | 3/2007 | Edidin et al. |
| 2007/0049935 A1 | 3/2007 | Edidin et al. |
| 2007/0050034 A1 | 3/2007 | Schwardt et al. |
| 2007/0050035 A1 | 3/2007 | Schwardt et al. |
| 2007/0055201 A1 | 3/2007 | Seto et al. |
| 2007/0055237 A1 | 3/2007 | Edidin et al. |
| 2007/0055246 A1 | 3/2007 | Zucherman et al. |
| 2007/0055265 A1 | 3/2007 | Schaller |
| 2007/0055266 A1 | 3/2007 | Osorio et al. |
| 2007/0055267 A1 | 3/2007 | Osorio et al. |
| 2007/0055271 A1 | 3/2007 | Schaller |
| 2007/0055272 A1 | 3/2007 | Schaller |
| 2007/0055273 A1 | 3/2007 | Schaller |
| 2007/0055274 A1 | 3/2007 | Appenzeller et al. |
| 2007/0055275 A1 | 3/2007 | Schaller |
| 2007/0055276 A1 | 3/2007 | Edidin |
| 2007/0055277 A1 | 3/2007 | Osorio et al. |
| 2007/0055278 A1 | 3/2007 | Osorio et al. |
| 2007/0055281 A1 | 3/2007 | Osorio et al. |
| 2007/0055284 A1 | 3/2007 | Osorio et al. |
| 2007/0055300 A1 | 3/2007 | Osorio et al. |
| 2007/0060933 A1 | 3/2007 | Sankaran et al. |
| 2007/0060935 A1 | 3/2007 | Schwardt et al. |
| 2007/0067034 A1 | 3/2007 | Chirico et al. |
| 2007/0068329 A1 | 3/2007 | Phan et al. |
| 2007/0073292 A1 | 3/2007 | Kohm et al. |
| 2007/0078436 A1 | 4/2007 | Leung et al. |
| 2007/0078463 A1 | 4/2007 | Malandain |
| 2007/0093689 A1 | 4/2007 | Steinberg |
| 2007/0093899 A1 | 4/2007 | Dutoit et al. |
| 2007/0093906 A1 | 4/2007 | Hudgins et al. |
| 2007/0123986 A1 | 5/2007 | Schaller |
| 2007/0135922 A1 | 6/2007 | Trieu |
| 2007/0149978 A1 | 6/2007 | Shezifi et al. |
| 2007/0150059 A1 | 6/2007 | Ruberte et al. |
| 2007/0150060 A1 | 6/2007 | Trieu |
| 2007/0150061 A1 | 6/2007 | Trieu |
| 2007/0150063 A1 | 6/2007 | Ruberte et al. |
| 2007/0150064 A1 | 6/2007 | Ruberte et al. |
| 2007/0162127 A1 | 7/2007 | Peterman et al. |
| 2007/0167945 A1 | 7/2007 | Lange et al. |
| 2007/0168038 A1 | 7/2007 | Trieu |
| 2007/0179612 A1 | 8/2007 | Johnson et al. |
| 2007/0179615 A1 | 8/2007 | Heinz et al. |
| 2007/0179616 A1 | 8/2007 | Braddock, Jr. et al. |
| 2007/0179618 A1 | 8/2007 | Trieu et al. |
| 2007/0185578 A1 | 8/2007 | O'Neil et al. |
| 2007/0191953 A1 | 8/2007 | Trieu |
| 2007/0197935 A1 | 8/2007 | Reiley et al. |
| 2007/0198025 A1 | 8/2007 | Trieu et al. |
| 2007/0208426 A1 | 9/2007 | Trieu |
| 2007/0213717 A1 | 9/2007 | Trieu et al. |
| 2007/0233074 A1 | 10/2007 | Anderson et al. |
| 2007/0260255 A1 | 11/2007 | Haddock et al. |
| 2007/0270957 A1 | 11/2007 | Heinz |
| 2007/0282443 A1 | 12/2007 | Globerman et al. |
| 2008/0021557 A1 | 1/2008 | Trieu |
| 2008/0027437 A1 | 1/2008 | Johnson et al. |
| 2008/0027453 A1 | 1/2008 | Johnson et al. |
| 2008/0027454 A1 | 1/2008 | Johnson et al. |
| 2008/0071356 A1 | 3/2008 | Greenhalgh et al. |
| 2008/0154272 A1 | 6/2008 | Schaller et al. |
| 2008/0177306 A1 | 7/2008 | Lamborne et al. |
| 2008/0195210 A1 | 8/2008 | Milijasevic et al. |
| 2008/0281364 A1 | 11/2008 | Chirico et al. |
| 2009/0018524 A1 | 1/2009 | Greenhalgh et al. |
| 2009/0105775 A1 | 4/2009 | Mitchell et al. |
| 2010/0082033 A1 | 4/2010 | Germain |
| 2010/0241177 A1 | 9/2010 | Schaller et al. |
| 2010/0262242 A1 | 10/2010 | Chavatte et al. |
| 2010/0298832 A1* | 11/2010 | Lau et al. .................. 606/80 |
| 2012/0239050 A1 | 9/2012 | Linderman et al. |
| 2012/0330314 A1 | 12/2012 | Schaller et al. |
| 2013/0006232 A1 | 1/2013 | Pellegrino |

FOREIGN PATENT DOCUMENTS

| | | |
|---|---|---|
| EP | 0529275 A2 | 3/1993 |
| EP | 0 621 020 A1 | 10/1994 |
| EP | 1 157 676 A1 | 4/2001 |
| EP | 1157676 A1 | 11/2001 |
| FR | 2586183 | 2/1987 |
| FR | 2712486 A1 | 5/1995 |
| FR | 2 913 331 | 12/2008 |
| WO | WO 93/04634 | 3/1993 |
| WO | WO 00/67650 | 11/2000 |
| WO | WO 00/67651 | 11/2000 |
| WO | WO 02/17824 A2 | 3/2002 |
| WO | WO 02/30338 A1 | 4/2002 |
| WO | WO 02/43628 A1 | 6/2002 |
| WO | WO 02/47563 A1 | 6/2002 |
| WO | WO 02/071921 A2 | 9/2002 |
| WO | WO 03/007854 A1 | 1/2003 |
| WO | WO 03/020169 A2 | 3/2003 |
| WO | WO 03/022165 A1 | 3/2003 |

(56) References Cited

FOREIGN PATENT DOCUMENTS

| | | |
|---|---|---|
| WO | WO 03/028587 A2 | 4/2003 |
| WO | WO 03/059180 A2 | 7/2003 |
| WO | WO 03/101308 A1 | 12/2003 |
| WO | WO2004/034924 A2 | 4/2004 |
| WO | WO 2004/062505 A1 | 7/2004 |
| WO | WO 2004/098420 A2 | 11/2004 |
| WO | WO 2004/108022 A1 | 12/2004 |
| WO | WO 2005/032433 A2 | 4/2005 |
| WO | WO 2005/051246 A2 | 6/2005 |
| WO | WO 2005/081877 A2 | 9/2005 |
| WO | WO 2006/047645 A2 | 5/2006 |
| WO | WO 2006/060420 A1 | 6/2006 |
| WO | WO 2006/066228 A2 | 6/2006 |
| WO | WO 2007/022194 | 2/2007 |
| WO | WO2007/067726 A2 | 6/2007 |
| WO | WO 2008103781 A2 | 8/2008 |

OTHER PUBLICATIONS

Annex to PCT Invitation to Pay Additional Fees, Re: International application No. PCT/US2006/031861 dated Jan. 15, 2007.

PCT Notification concerning transmittal of International Preliminary report on patentability and PCT Written Opinion of the International Searching Authority, PCT Application No. US2006/031861 dated Feb. 28, 2008.

Edeland, H.G., "Some Additional Suggestions for an Intervetebral Disc Prosthesis", J of BioMedical Engr., vol. 7(1) pp. 57-62, Jan. 1985.

Notification of Transmittal of International Search Report, International Search Report and Written Opinion for PCT/US2012/043760 dated Jan. 3, 2013.

* cited by examiner

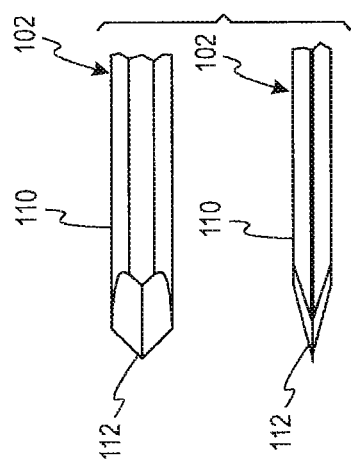
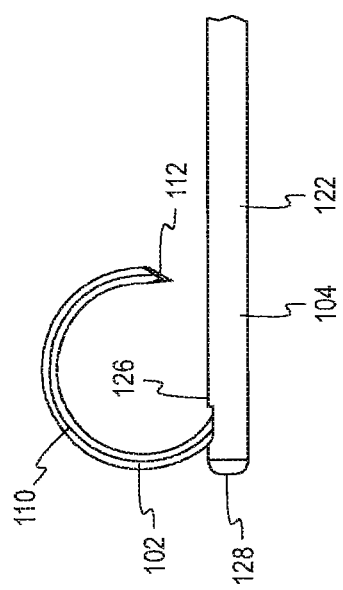
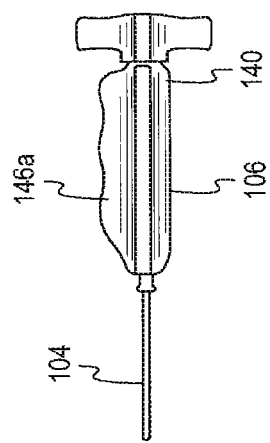
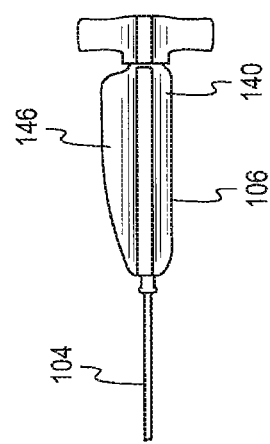

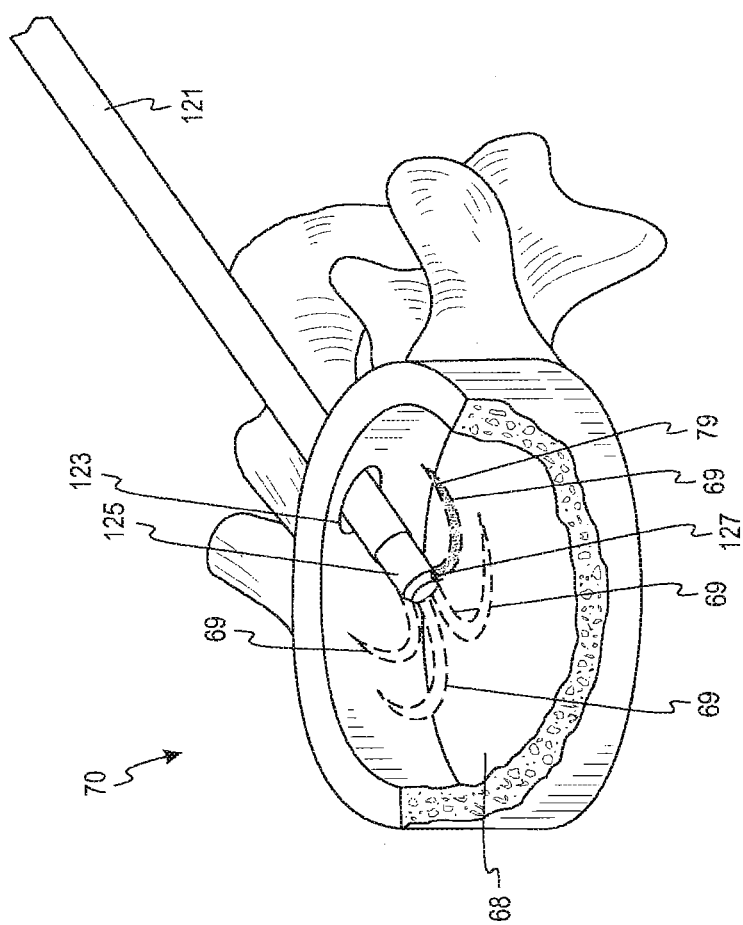

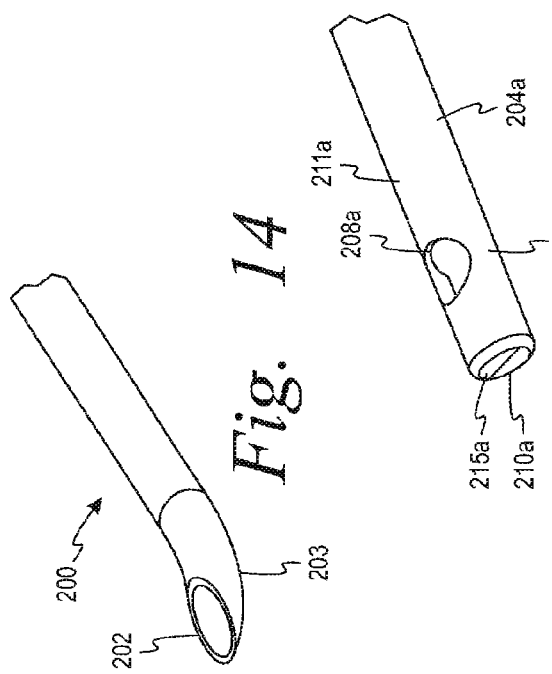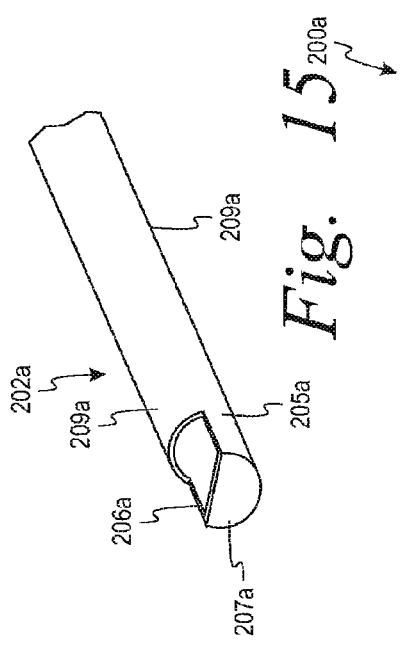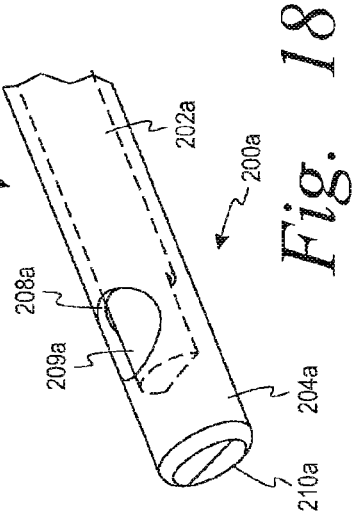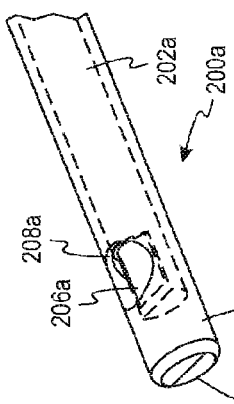

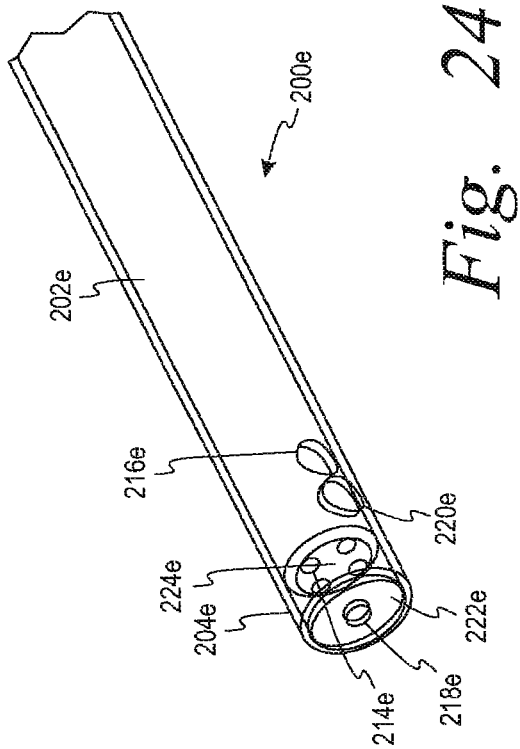
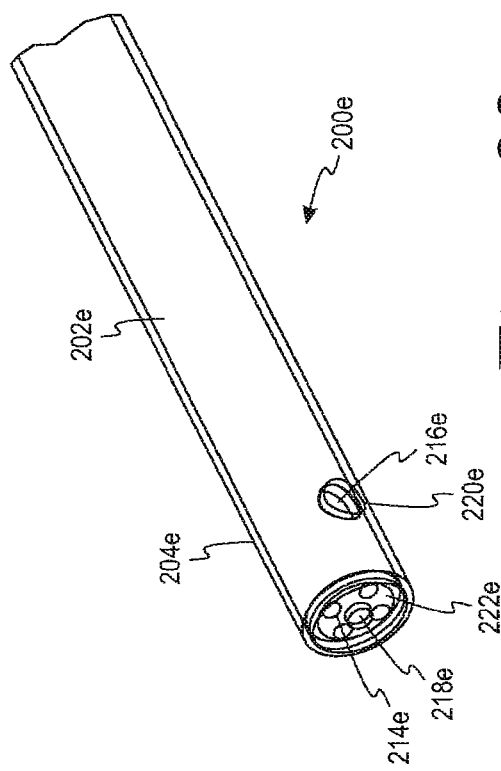

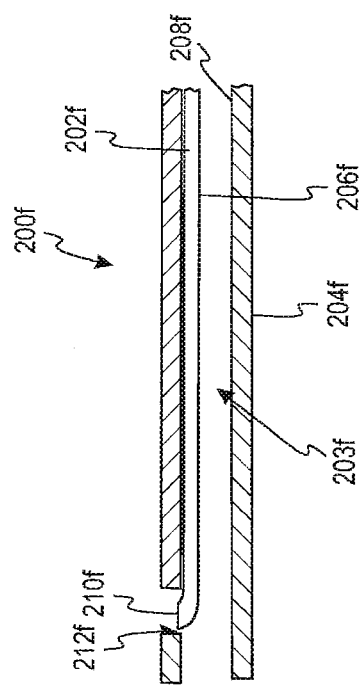

DEVICES AND METHODS FOR TREATING BONE TISSUE

This application is a continuation of U.S. patent application Ser. No. 13/530,415, filed Jun. 22, 2012, which claims the benefits of U.S. Provisional Patent Application No. 61/500,929, filed Jun. 24, 2011, both of which are incorporated herein by reference.

BACKGROUND

The present disclosure generally relates to devices and methods for the treatment of bone conditions and, more particularly, to devices and methods for forming channels within bone tissue and devices and methods for delivering bone filler material within bone tissue.

Bones or portions of bones often comprise an outer relatively hard layer referred to as cortical bone and inner material referred to as cancellous bone. A variety of physical conditions can cause cancellous bone to become diseased or weakened. Such conditions can include, for example, osteoporosis, avascular necrosis, cancer or trauma. Weakened cancellous bone can result in an increased risk of fracture of the cortical bone surrounding the cancellous bone, because the diseased or weakened cancellous bone provides less support to the exterior cortical bone than healthy cancellous bone.

One common condition that is caused by diseased or damaged cancellous bone is vertebral compression fractures. A vertebral compression fracture is a crushing or collapsing injury to one or more vertebrae. One of the leading causes, but not an exclusive cause, of vertebral compression fractures is osteoporosis. Osteoporosis reduces bone density, thereby weakening bones and predisposing them to fracture. The osteoporosis-weakened vertebrae can collapse during normal activity and are also more vulnerable to injury from shock, trauma or other forces acting on the spine. In severe cases of osteoporosis, actions as simple as bending can be enough to cause a vertebral compression fracture.

While the vertebral compression fractures may heal without intervention, the crushed bone may fail to heal adequately. Moreover, if the bones are allowed to heal on their own, the spine may be deformed to the extent the vertebrae were compressed by the fracture. Spinal deformity may lead to other adverse conditions, such as, breathing and gastrointestinal complications, and adverse physical effect on adjacent vertebrae.

Minimally invasive surgical techniques for treating vertebral compression fractures are becoming more and more common. One such technique used to treat vertebral compression fractures is injection of bone filler material into the fractured vertebral body. This procedure is commonly referred to as percutaneous vertebroplasty. More specifically, vertebroplasty involves inserting an injection needle into bone material in the vertebra and injecting bone filler material (for example, bone cement, allograph material or autograph material) into the collapsed vertebra to stabilize and strengthen the crushed bone.

Another type of treatment for vertebral compression fractures is known as Kyphoplasty. Kyphoplasty is a modified vertebroplasty treatment that uses one or more balloons, introduced into the vertebra. First a cannula or other device is inserted into the vertebra. The cannula may have one or more balloons associated with it or another device may be inserted with balloons. As the balloons are inflated, the balloons push the cancellous bone outwardly, crushing or compacting the cancellous bone to create a cavity, which significantly alters the natural structure of the cancellous bone. The balloons are then deflated and removed, leaving a cavity. Bone cement is injected into the cavity to stabilize the fracture.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a method for creating channels within cancellous bone of a vertebral body includes traversing an elongated member through cancellous bone of a vertebral body along a first generally non-linear path. The elongated member is retracted along the first generally non-linear path, thereby leaving a first generally non-linear channel. The elongated member is traversed through the cancellous bone of the vertebral body along a second generally non-linear path, which second path does not completely coincide with the first path, and then the elongated member is retracted along the second generally nonlinear path, thereby leaving a second generally non-linear channel. Optionally, bone filler material is deployed into the channels. In one embodiment, the bone filler material is substantially directed into the channels and may be separately directed into the individual channels.

In another aspect, a method of treating a vertebral body includes positioning at least a distal end portion of a cannula within a vertebral body. The distal end portion includes an opening therein and an elongated member located within the cannula. At least a distal end portion of the elongated member is deployed out of the opening in the distal end portion of the cannula and through bone structure of the vertebral body along a first path to form a first generally non-linear channel in the bone structure. The distal end portion of the elongated member is retracted into the cannula, and at least the distal end portion of the elongated member is redeployed out of the opening in the distal end portion of the cannula and through bone structure of the vertebral body in a second path to form a second generally non-linear channel, wherein the second channel does not completely coincide with the first channel. Optionally, bone filler material is deployed into the channels. In one embodiment, the bone filler material is substantially directed into the channels and may be separately directed into the individual channels.

In yet another aspect, a device for creating channels within bone tissue includes a housing and a cannula extending from the housing and sized for insertion into bone tissue. The cannula includes a proximal end portion and a distal end portion wherein the proximal end portion is rotatably connected to the housing such that the cannula and the housing are rotatable relative to one another. The device also includes an elongated member for creating channels within bone tissue and positioned within the cannula. The elongated member has a first generally linear configuration and a portion that is selectively advanceable out of and retractable into an opening in the distal end portion of the cannula. The portion of the elongated member extending from the opening in the distal end of the cannula has a second generally non-linear configuration.

In yet a further aspect, a device for creating channels within bone tissue and delivering bone filler within bone tissue includes a housing and a cannula extending from the housing and sized for insertion into bone tissue. The cannula includes a proximal end portion and a distal end portion. The device also includes an elongated channel forming member positioned within the cannula and having a first generally linear configuration. The elongated member is selectively movable within the cannula so as to advance a portion of the elongated member out of and retract the portion of the elongated member into an opening in the distal end portion of the cannula. The portion of the elongated member advanced out of the opening in the distal end portion of the cannula forms a second generally non-linear configuration as it traverses through bone structure to form a channel in the bone structure. The elongated member also includes a passageway sized and configured to allow the bone filler to flow therethrough and into the channel created within the bone structure.

In yet a further aspect, a system for creating channels within bone tissue and delivering bone filler within bone tissue wherein the system includes a housing and a cannula extending from the housing. The cannula including a proximal end portion and a distal end portion. An elongated member for creating channels within bone tissue is positioned within the cannula. The elongated member has a first generally linear configuration and a portion that is selectively advanceable out of and retractable into an opening in the distal end portion of the cannula. The portion of the elongated member extending from the opening in the distal end of the cannula has a second generally non-linear configuration. The system also includes a bone filler material delivery member for delivering bone filler material into the channel, wherein the bone filler material delivery member selectively delivers bone filler material in a generally axial and a general radial direction.

In still a further aspect, a device for selectively delivering bone filler including an outer cannula having a longitudinal axis and an inner cannula movably positioned at least partially within the outer cannula. The inner cannula is sized and configured to allow bone filler to flow therethrough and out of a distal end portion of the inner cannula. The inner cannula is selectively positioned in a first configuration relative to the outer cannula wherein bone filler exits the outer cannula in a first generally radial direction relative to the longitudinal axis of the outer cannula, and the inner cannula being selectively positioned in a second configuration relative to the outer cannula wherein bone filler exits the outer cannula in a second generally axial direction generally parallel to the longitudinal axis of the outer cannula.

BRIEF DESCRIPTION OF THE DRAWINGS

In the course of this description, reference will be made to the accompanying drawings, wherein:

FIG. 6 is a partial side view of the elongated member exiting the a distal end opening of the cannula of the channeling device of FIG. 3;

FIG. 7 are partial side views of one embodiment of the distal tip of an elongated member of the present disclosure;

FIG. 8 is a side view of an alternative housing of a channeling device of the present disclosure;

FIG. 9 is a side view of an alternative housing of a channeling device of the present disclosure;

FIG. 12f is a perspective view of the vertebral body of FIG. 12e shown with a bone filler delivery device delivering bone filler into a channel;

FIG. 14 is a perspective view of one embodiment of a bone filler delivery conduit;

FIG. 15 is a perspective view of the inner cannula of another embodiment of a bone filler delivery conduit;

FIG. 16 is a perspective view of the outer cannula of the bone filler delivery conduit;

FIG. 17 is a perspective view of the bone filler delivery conduit shown in a first configuration;

FIG. 18 is a perspective view of the bone filler delivery conduit of FIG. 17 shown in a second configuration;

FIG. 23 is a perspective view of another embodiment of a bone filler delivery conduit shown in a first configuration;

FIG. 24 is a perspective view of the bone filler delivery conduit of FIG. 23 shown in a second configuration; and FIG. 25 is a cross-sectional view of another embodiment of a bone filler delivery conduit.

Corresponding reference numerals indicate corresponding parts throughout the several views.

DETAILED DESCRIPTION

Although detailed embodiments of the present subject matter are disclosed herein, it is to be understood that the disclosed embodiments are merely exemplary, and the subject matter may be embodied in various forms. Therefore, specific details disclosed herein are not to be interpreted as limiting the subject matter claimed, but merely as examples to illustrate and describe the subject matter and various aspects thereof.

As pointed out earlier, the present disclosure pertains to devices and methods for forming one or more passageways or channels in bone tissue and devices and methods for delivering bone filler material within bone tissue. The devices and methods will be described by way of example, but not limitation, in relation to procedures within the vertebral body. The apparatus and methods disclosed herein may be used to treat bone tissue in other areas of the body as well, for example, in other skeletal bone locations, such as the tibia, femur and others, which may have significantly denser bone than that in a vertebral body. The devices and methods of use thereof also can be used to deliver bone filler material in bone tissue for virtually any purpose or procedure where such passageways or channels are desired.

Figure 1:
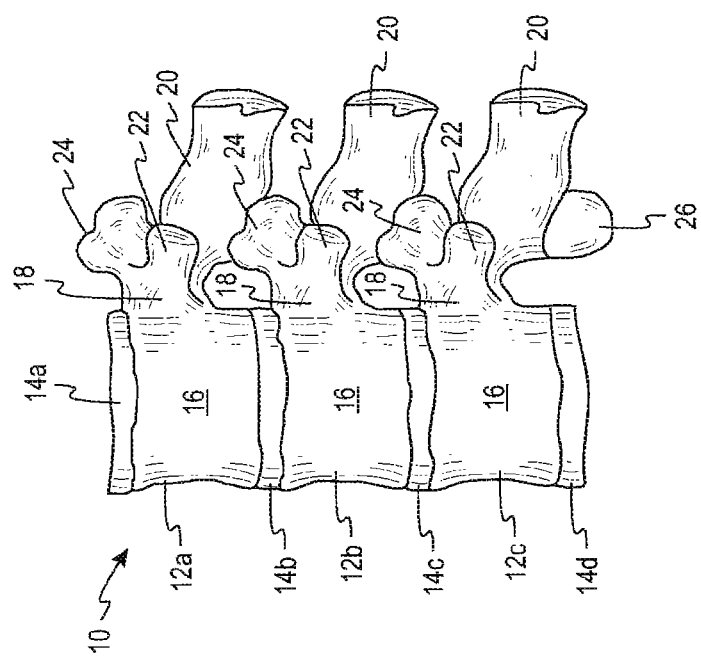
FIG. 1 is a partial side view of a normal human vertebral column.

FIG. 1 illustrates a section of a healthy vertebral (spinal) column, generally designated as 10, free of injury. The vertebral column 10 includes adjacent vertebrae 12a, 12b and 12c and intervertebral disks 14a, 14b, 14c and 14d separating adjacent vertebrae. The vertebrae, generally designated as 12, include a vertebral body 16 that is roughly cylindrically shaped and comprised of spongy inner cancellous bone surrounded by compact bone (referred to as the cortical rim). The body 16 of the vertebra 12 is capped at the top by a superior endplate (not shown) and at the bottom by an inferior endplate (not shown) made of a cartilaginous layer. On either side of the vertebral body 16 are the pedicles 18, which lead to the spinal process 20. Other elements of the vertebra include the transverse process 22, the superior articular process 24 and the inferior articular process 26.

In vertebral compression fractures the vertebral body may be fractured from trauma, such as impact (even if healthy), or suffer fractures that result from weakening of the cortical rim such as from osteoporosis. When weakened by osteoporosis, the vertebra is increasingly subject to fracture due to routine forces from standing, bending or lifting.

Figure 2:
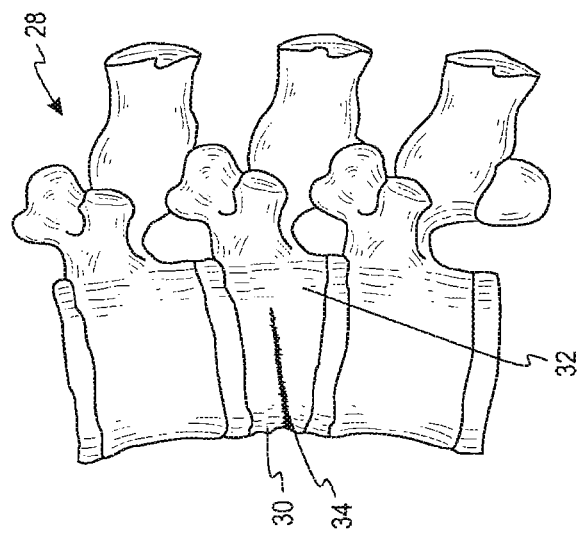
FIG. 2 is comparable to FIG. 1, depicting a vertebral compression fracture in one of the vertebral bodies.

FIG. 2 illustrates a damaged vertebral column, generally designated as 28, with a vertebral body 30 of a vertebra 32 suffering from a compression fracture 34. The vertebral body 30 suffering from the compression fraction 34 becomes somewhat wedge shaped and reduces the height of both the vertebra 32 and vertebral column 28 on the anterior (or front) side. As a result, this reduction of height can affect the normal curvature of the vertebral column 28. If left untreated, the vertebral body may further collapse and fracture causing additional pain and complications.

Turning now to a detailed description of illustrated embodiments described herein.

I. Channel Creation Device

Figure 3:
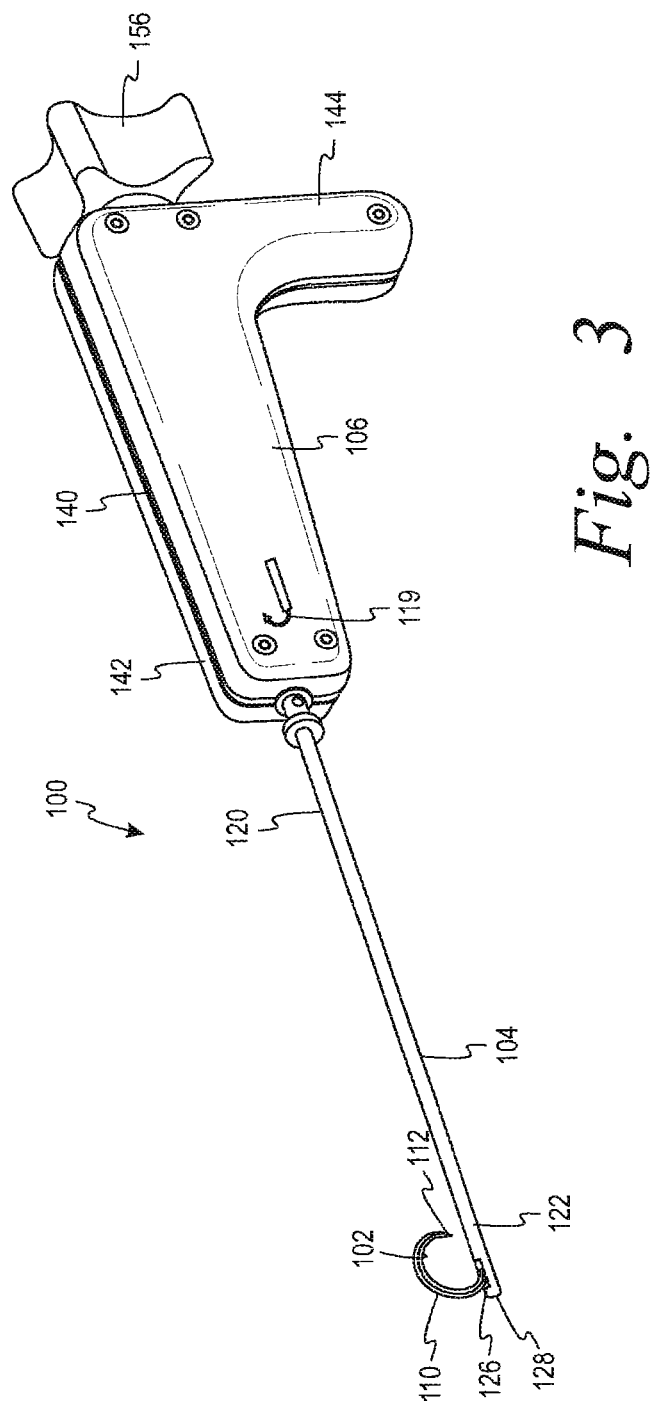
FIG. 3 is a perspective view of one embodiment of a channeling device of the present disclosure.

FIG. 3 illustrates one embodiment of a channel creation device 100 of the present disclosure. Generally, the device includes three components: an elongated member 102, a cannula 104, and a housing 106. The channel creation devices of the present disclosure may be used to create channels or passageways in a variety of configurations including but not limited to arcuate configurations, such as arced or looped configurations. The device has the capability of being oriented in a variety of orientations within the bone tissue to create channels in any multitude of directions and to create a variety of multi-channel patterns or configurations.

i. Elongated Member

Elongated member 102 may be an elongated bone tamp. Bone tamps per se are not new, and the term generally refers to a device with an elongated shaft for insertion into bone. Such bone tamps were known long before the development of vertebroplasty and kyphoplasty. The bone tamps of the present disclosure are referred to as a bone tamp because they are inserted into bone tissue, forming a passageway or channel therethrough by reason of its insertion, just as bone tamps have done since their early development.

In one embodiment, elongated member 102 is comprised of an elongated body 110, such as a shaft, wire, thread or ribbon, having a rectangular cross-section. In other embodiments, elongated body 110 can have a variety of cross-sectional shapes and profiles, such as round or other simple and complex geometric profiles.

Elongated member 102 can be comprised of any suitable material and in one embodiment is comprised of a biocompatible shape memory material. The shape memory material can be any suitable material, in which the shape of elongated member 102 can be changed upon application of external force, and which substantially returns to its initial shape upon remove of the external force. Such shape memory materials can include, for example, Nitinol (NiTi) or other suitable alloy (Cu—Al—Ni, Ti—Nb—Al, Au—Cd, etc.) or a shape memory polymer.

In its initial configuration, elongated member 102 has an arcuate configuration including but not limited to a loop, partial loop, multiple loops, partial curve, circle, oval, elliptical, helical, spiral, planar or non-planar curved configurations or other shape with varying curvature that is suitable for the tissue being treated and the desired procedure. For example, the arcuate configuration may be a planar loop or partial loop or arc. The arcuate configuration also may be a planar spiral that includes multiple loops in substantially the same plane or the configuration may be a helical configuration including a plurality of vertically adjacent loops or windings.

Elongated member 102 may be constrained into a generally linear or straight configuration for passage through cannula 104. As illustrated in FIG. 6, when elongated member 102 exits opening 126 in distal end portion 122 of cannula 104, the elongated member returns to its initial arcuate configuration. In one embodiment, the initial configuration of elongated member 102 is an arc with an outer diameter of 20 mm. This size is typically appropriate for spanning the entire lateral width of most vertebral bodies in most adult patients. However, in other embodiments, the arc diameter may range from about 10 mm to about 30 mm or more. The arcuate shape may have a constant or varying diameter so as to achieve the desired configuration for the tissue being treated. The arcuate shape may be about ¾ of a loop in one embodiment, but may range from about ¹⁄₁₀ of a loop to multiple loops, depending upon the number and size of the channels desired.

Referring to FIGS. 6 and 7, the elongated member 102 preferably has a distal end portion 112 that is configured to optimize the elongated member's penetration through tissue and more particularly, through dense bone tissue. As illustrated in FIG. 7, distal end portion 112 of elongated member 102 may have a 4-faceted bevel configuration that may be referred to as a "double-diamond" configuration. However it shall be appreciated that many other tip configurations may be suitable as well, including single, double, or triple bevels so as to facilitate tip penetration and trajectory as the elongated member is advanced through bone tissue. The angle of the bevels may be varied as well to achieve the optimal balance between the tip strength and penetration capability.

In one embodiment, the geometric shape of the cross section of elongated member 102 is rectangular, with outer dimensions of about 0.055 inches by about 0.087 inches with the longer dimension aligned perpendicular to the plane of the loop formed by the elongated member. The primary outer dimension could range from about 0.010 inches to about 0.250 inches, depending upon the application, the size of the tissue being treated, and the desired stiffness of elongated member. It will be appreciated that the geometric shape of the cross section of the elongated member 102 could include circular, tubular, flat-rectangles, c-shaped, u-shaped, I-beams or any other suitable shape. In some procedures, elongated member 102 may be deployed and retracted multiple times into tissue, either along the same path or along different paths. For such procedures, the cross-sectional shape and size should be such that the elongated member has sufficient strength to undergo multiple deployments and retractions within bone tissue.

Further disclosure of one embodiment of a suitable elongated member can be found in co-owned U.S. application Ser. No. 12/020,396; filed Jan. 25, 2008 and published as U.S. Patent Publication No. 2008/0154272, which is incorporated herein by reference in its entirety.

ii. Cannula

Figure 4:
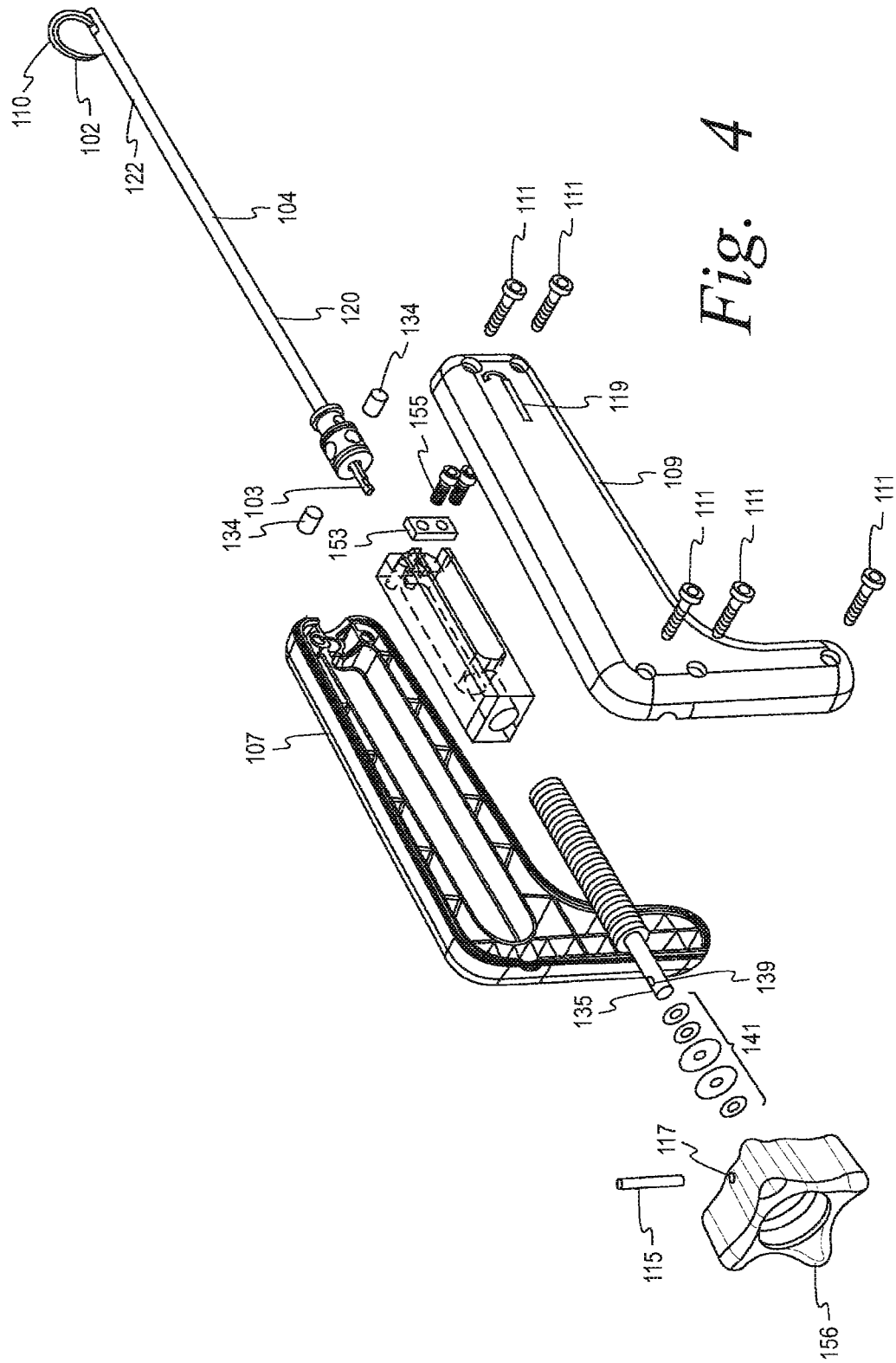
FIG. 4 is an exploded perspective view of the channeling device of FIG. 3.
Figure 5:
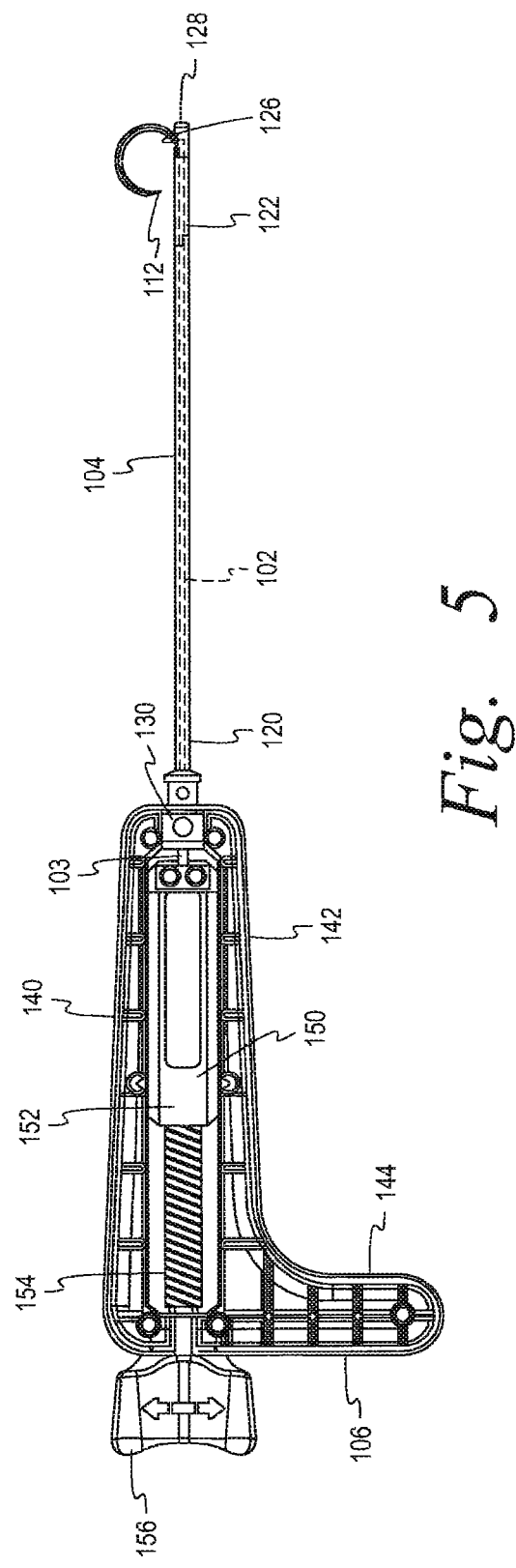
FIG. 5 is a cross-sectional view of the channeling device of FIG. 3.

Referring to FIGS. 3-5, cannula 104 may have an elongated generally cylindrical shape and includes a proximal end portion 120 and distal end portion 122. Preferably, the length of the cannula 104 is sufficient to place the distal end portion 122 of the cannula 104 at a desired location within a patient. Accordingly, the length of the cannula 104 may vary depending on the particular procedure, location of treatment and the condition to be treated. In one embodiment, which is well suited for transpedicular access to most vertebral bodies for most patients, the cannula has a working length of about 17 cm. In other embodiments, the length of the cannula may range from about 5 mm to about 25 cm.

Cannula 104 includes an interior lumen (not shown) sized for receiving elongated member 102 therethrough. The cross-sectional width of the interior lumen and the outer cross-sectional width of cannula 104, which can be diameters when the cannula has a generally circular cross-sectional shape, can vary greatly depending on the type of procedure and the size of the elongated member used. When used in minimally invasive surgical procedures, the cannula 104 is preferably sized to be inserted through a relatively small access hole or site. Thus, the cross-sectional width of the interior lumen and the outer cross-sectional width of the cannula 104 are preferably no larger than what is require to allow passage of elongated member 102 through cannula 104. In one embodiment, the outer diameter of the cannula is between about 4 mm; however, in other embodiments, the outer diameter of the cannula may range from about 2 mm to about 5 mm.

The distal end portion 122 of cannula 104 includes an opening 126 that communicates with the interior lumen. In the illustrated embodiment, the distal tip 128 of cannula 104 is closed and the opening 126 is located in a sidewall of the cannula 104. In an alternative embodiment, opening 126 can be located in distal tip 128 or both the sidewall and the distal tip. Opening 126 at the distal end portion 122 of cannula 104 is sized to allow the elongated member 102 to exit the cannula 104 through the opening 126 and into bone tissue or structure.

Cannula 104 may be comprised of any suitable material and is preferably constructed out of a surgical grade of steel that can resist the mechanical forces generated during movement of the elongated member therethrough. Cannula 104 also may be resterilized for multiple use. In the illustrated embodiment, elongated member 102 exits the cannula through opening 126 (see FIG. 6). As mentioned above, elongated member 102 may be deployed and retracted multiple times during a procedure and cannula 104 may be constructed for multiple use. As such, the repeated deployment of elongated member 102 may result in wear at the exit point of the cannula due to interaction, e.g. contact, between the elongated member and cannula. Thus, distal end portion 122 of cannula 104 at and/or near opening 126 may be made of materials such as ceramics, plastics, or other biocompatible engineering materials that are wear resistant.

iii. Housing

As illustrated in FIG. 3, housing 106 of channel creation device 100 is preferably, but not necessarily, configured to be handheld so that the user can manually facilitate control and positioning of the cannula 104 during use. Housing 106 may be constructed from any suitable material, such as stainless steel, plastic or the like. In the illustrated embodiment, housing 106 generally includes a body portion 140 that includes first and second halves 107 and 109, respectively, which are secured together by screws 111 as shown in FIG. 4. First and second halves 107 and 109 may be held together by other means, such as adhesive.

In one embodiment, the body portion 140 is sized and shaped for convenient grasping or holding by a user. In the embodiment shown in FIG. 3, the body portion 140 has a "gun" handle shape, more specifically, the body portion includes a main portion 142 and a handle 144 that extends form the main portion 142. However, other configurations or contours of the body portion 140, preferably those that provide for ergonomic convenience, may also be used. For example, FIGS. 8 and 9 illustrate alternate embodiments where a smooth fin 146 or ribbed fin 146a is attached to the body portion 140 for gripping the housing. In one embodiment fin 146 is aligned with opening 126 in the distal end portion 122 of cannula 104 to indicate the orientation of the opening 126 without the need to require x-ray imaging.

Referring to FIG. 5, body portion 140 of housing 106 houses a drive mechanism 150 that is used to advance and retract the elongated member 102 through cannula 104 and more specifically out of and into the opening 126 in the distal end portion 122 of the cannula 104. In the embodiment shown, drive mechanism 150 is what is commonly referred to as a "screw-and-carriage" design, however, other drive mechanisms may be used. For example, the drive mechanism may be rack-and-pinion, or ratcheting mechanisms such as those used in caulking guns.

Figure 10:
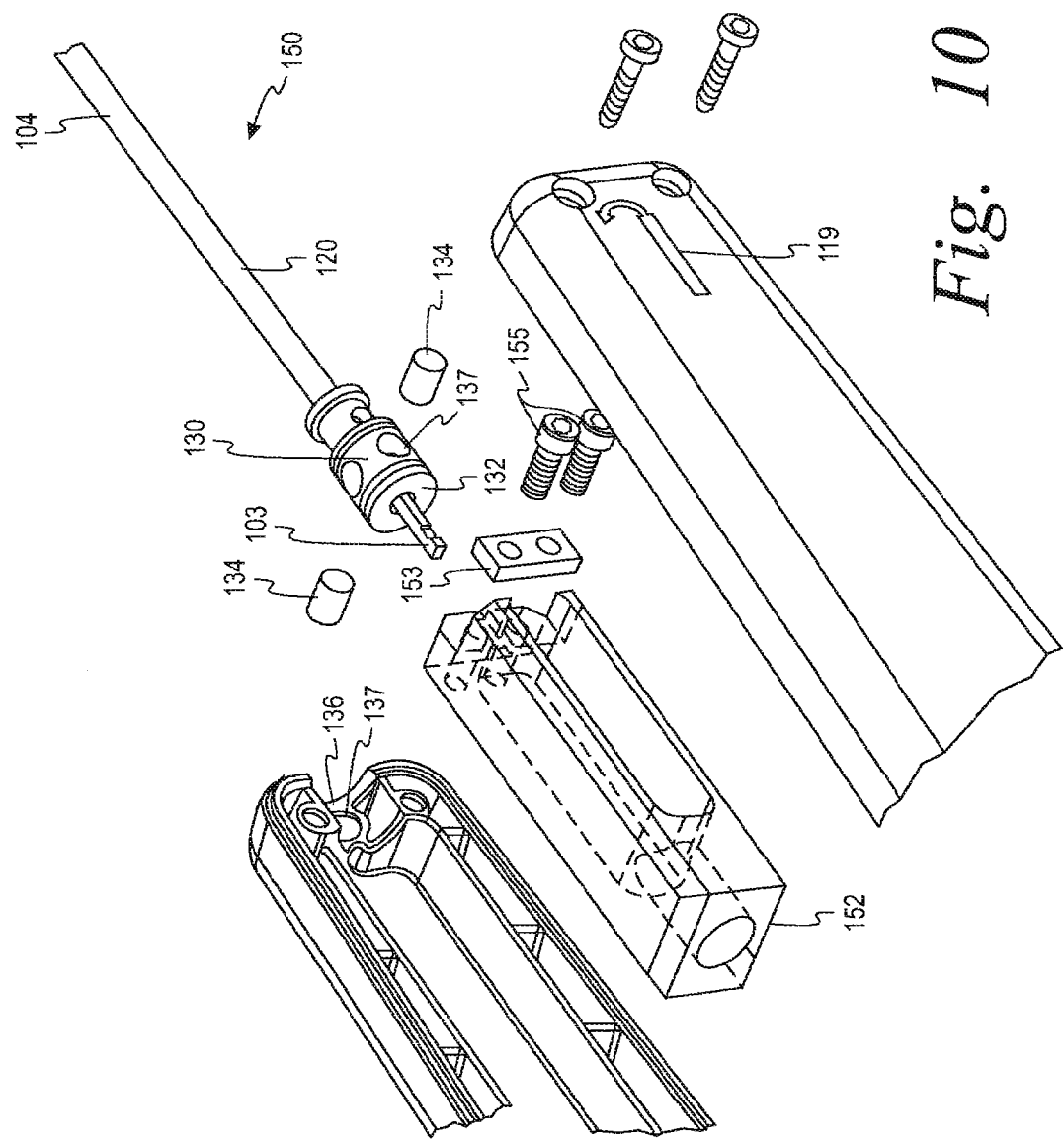
FIG. 10 is an enlarged exploded partial view of one embodiment of the channeling device.
Figure 11:
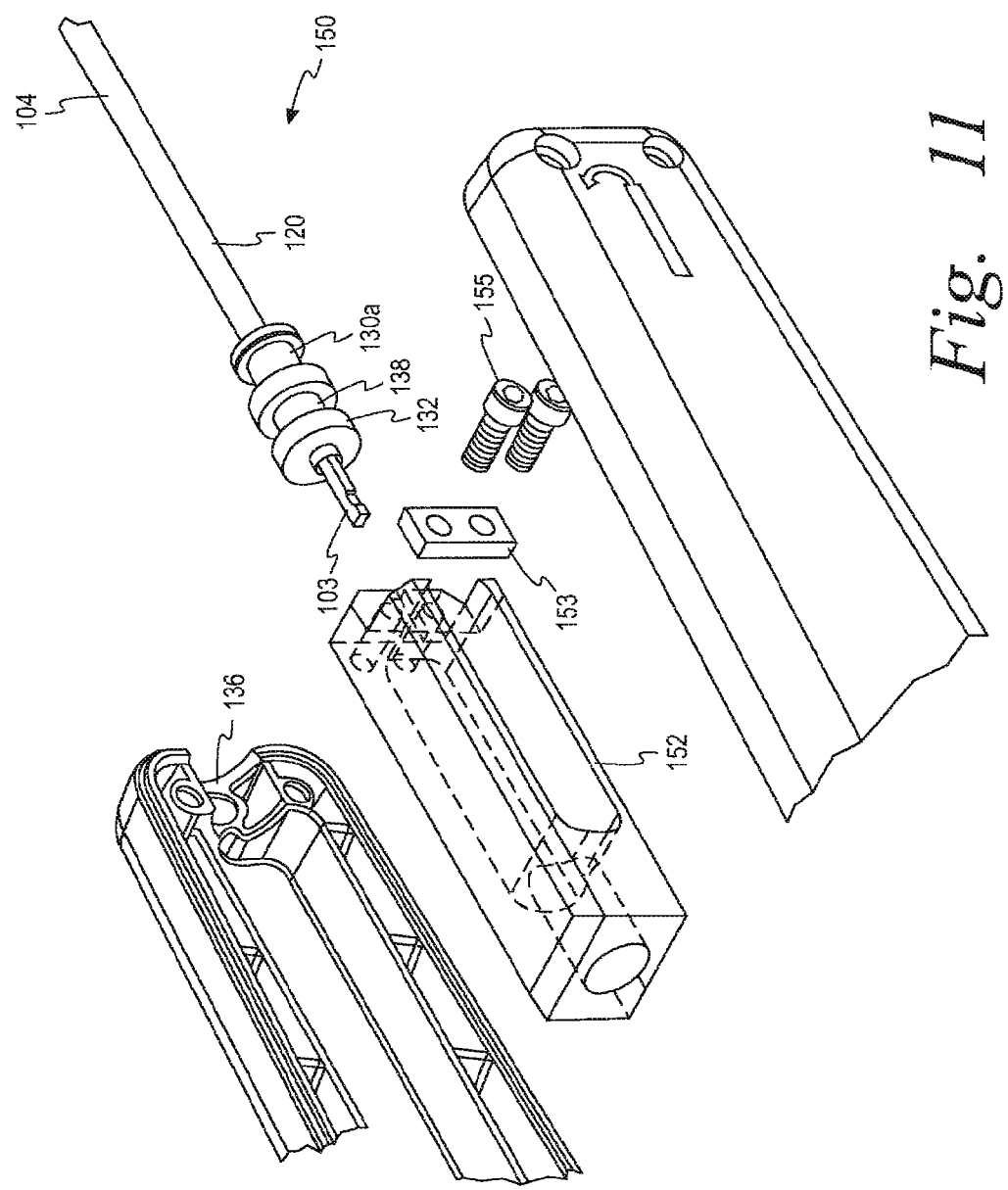
FIG. 11 is an enlarged exploded partial view of an alternative embodiment of the channeling device.

Drive mechanism 150 shown in FIG. 5 includes a carriage 152 that translates back and forth along a screw shaft 154 as the screw shaft is rotated. The proximal end 103 of elongated member 102 is connected to carriage 152. For example, proximal end 103 of elongated member 102 may be clamped onto carriage 152. As shown in FIGS. 10 and 11, the proximal end 103 of elongated member 102 may be clamped to carriage 152 with plate 153 and screws 155, however, it will be appreciated that any other connection means may be used.

Referring back to FIGS. 4 and 5, proximal end 135 of the screw shaft 154 may extend out of housing 106. As illustrated in FIG. 4, a pin 115 is inserted into opening 117 of drive knob 156 and through opening 139 in proximal end 135 of screw shaft 154. Washers 141 may be located on proximal end 135 of screw shaft 154 on either side of the housing. Drive knob 156 may be selectively rotated by the user in order to rotate screw shaft 154. As screw shaft 154 rotates, carriage 152 translates along the screw shaft to advance or retract the elongated member 102. When desired, this drive mechanism allows generation of relatively high forces.

In one embodiment, screw shaft 154 is an acme thread form design in which a ratio of about six full revolutions by knob 156 translates into one full loop of deployment of elongated member 102. This aids in controlling the speed of deployment of elongated member 102. However, it will be appreciated that other thread forms, ratios, or speeds of deployment may be desirable. Images via x-ray or the like may be employed to assist in proper positioning and determining the reach elongated member 102 as it is deployed from cannula 104. Additionally, housing 106 may include a visual indicator 119 to indicate the direction and orientation of deployment of elongated member 102 from cannula 104. In the illustrated embodiment the visual indicator is an arrow indicating the direction of deployment, which arrow may be printed on the housing or an integral part of the housing. The visual indicator can take on other forms as well.

Cannula 104 is operably connected to housing 106. Referring to FIG. 5, optionally device 100 includes hub 130 that operably connects cannula 104 and housing 106 to one another. Hub 130 may be part of the cannula, part of the housing and a piece that is separate from the housing and the cannula. Hub 130 is an optional element and cannula 104 and housing 106 may be connected without hub 130. It is understood that the cannula and housing may be in a fixed relationship in which the cannula and housing are not movable relative to each other. Alternatively, housing and the cannula may rotate relative to each other.

FIG. 10 illustrates one embodiment wherein cannula 104 and housing 106 are in a fixed relationship both axially and rotationally. In this embodiment, device 100 includes optional hub 130 which has a barrel portion 132 that is sized to fit into a complementary recess 136 defined in the housing 106. In the illustrated embodiment, the hub 130 is fixedly attached to housing 106 using pins 134 that fit into recesses 137 defined in the barrel portion 132. When housing 106 is rotated, this construction transmits the torsional load directly to the cannula via the pins 134. It will be appreciated that other means of fixedly attaching hub 130 to housing 106 also may be used.

Device 100 also may be constructed such that cannula 104 and housing 106 rotate relative to one another. Cannula 104 and housing 106 may be rotatably connected to each other in any variety of different manners. Relative rotation between housing 106 and cannula 104 may assist in reducing unintentional or accidental rotation of the cannula 104 and elongated member 102 while such elements are deployed within the bone tissue or structure. For example, if housing 106 is accidentally or unintentionally rotated while cannula 104 and/or elongated member 102 are deployed within the bone tissue, relative rotation been housing 106 and cannula 104 allows the housing to rotate while cannula 104 and elongated member 102 remain stationary within the bone structure.

The rotatable connection between cannula 104 and housing 106 also may allow the housing to remain stationary while the cannula is rotated. For example, after cannula 104 has been deployed into bone structure but prior to deployment of the elongated member, the user may rotate the cannula relative to the housing and within the bone structure to position the cannula in a desired orientation while the housing remains stationary outside of the patient.

Referring to FIG. 11, when optional hub 130a is employed, hub 130a is adapted to allow housing 106 and cannula 104 to rotate relative to each other but resists axial translation. Hub 130a includes a notch 138 defined in barrel portion 132 that corresponds with a complimentary recess 136 within the housing 106 such that hub 130a rotates within recess 136. Alternatively, hub 130a may be stationary relative to housing 106, and cannula 104 may be rotatably connected to hub 130a such that cannula 104 rotates relative to housing 106 and hub 130a. In yet another embodiment, housing 106 and cannula 104 may both be rotatably connected to hub 130a. In yet another embodiment, the cannula may be rotationally connected to the housing without the use of hub 130a.

In certain instances, it may be desirable for there to be a desired amount of rotational resistance that prevents relative rotation between the housing and cannula until a sufficient amount of force is applied to overcome the resistance and initiate relative rotation between the housing and the cannula. The resistance to rotation may be provided by, for example, the connection between the cannula and housing, a function of the hub (when one is employed) or the elongated member.

In one example, rotational resistance is provided by torque resistance of elongated member 102. As mentioned above, in one embodiment, proximal end 103 of elongated member 102 is connected to drive mechanism 150 and more specifically to the carriage 152. When housing 106 is rotated by the user, instead of transmitting torsional loading to cannula 104, this embodiment translates the torsional loading directly to elongated member 102 via the clamping of the elongated member to carriage 152. When torsional loading is transmitted to elongated member 102, the portion of the elongated member 102 located inside the cannula is designed to twist under such loading, leaving the portion of cannula 104 and elongated member 102 deployed within the bone substantially stationary relative to the bone structure. The shape and size of the lumen of the cannula and/or opening 126 may be such that it is designed to allow a proximal end portion of elongated member 102 to twist while a distal end portion of elongated member 102 remains substantially stationary, e.g., does not twist. Elongated member 102 may be optimized to withstand such twisting via a selection of appropriate material and/or geometric profile that is designed to twist. Therefore, when housing 106 is rotated relative to the patient and sufficient resistance exists to prevent rotation of cannula 104 relative to the patient along with housing 106, e.g., cannula 104 and elongated member 102 are deployed in bone structure which creates resistance to rotation of the cannula relative to the bone structure, the proximal end portion of elongated member 102, in the illustrated embodiment, will twist allowing housing 106 to rotate and "slip" performing a clutching action along notch 138 defined in hub 130a and recess 136, resulting in housing 106 rotating relative to the patient and cannula 104 while cannula 104 remains substantially immobile relative to the bone structure of the patient.

The actual amount of reactive torque that is applied to twist elongated member 102 and thus allow housing 106 to rotate relative to cannula 104 depends upon many variables, such as the geometry of elongated member 102 within the cannula itself. For example, for a given material, if a larger cross-section is chosen, elongated member 102 may have larger torsional resistance and require more user torque to initiate rotation of housing 106 relative to elongated member 102. If a smaller cross-section is chosen using the same material, then elongated member 102 may have less torsional resistance and require less input torque to initiate rotation of housing 106 relative to cannula 104. The length of cannula 104, as well as relationship of the exposed or deployed length of elongated member 102 versus non-deployed length will also play a role in this mechanism for minimizing rotational displacement of the portion of the elongated member 102 extending out of opening 126 of cannula 104 and within the bone tissue.

Alternatively, proximal end portion 103 of elongated member 102 is rotatably connected to the drive mechanism. For example, proximal end portion 103 may be rotatably connected to carriage 152. When handle 106 is rotated relative cannula 104, the rotatable connections between the housing and cannula and between the carriage and elongated member allow housing 106 to rotate relative to cannula 104 and elongated member 102. The rotatable connection between the housing and cannula and/or the elongated member and drive mechanism may be constructed to provide some amount of desired resistance to rotation that must be overcome by a set amount of force to initiate rotation between the cannula and housing. The rotational resistance may be provided, for example, by fictional engagement between the cannula and the housing or the elongated member and the drive mechanism or as function of the hub, when one is employed.

II. Method of Use of Channeling Device

Referring to FIGS. 12a-12d, vertebral body 70 of vertebra 71 includes an interior region, which may include cancellous bone tissue 68, surrounded by cortical rim 63. The distal end portion 131 of a working or access cannula 133 is inserted into the interior region and the cancellous bone 68 of vertebral body 70 through a percutaneous transpedicular access port in cortical rim 63. Cannula 104 of the channeling device is inserted through access cannula 133 and into the interior of vertebral body 70.

The transpedicular access port into the interior region of the vertebral body can be made by using standard percutaneous transpedicular techniques that are well known in the art. Such standard techniques may include the use of minimally invasive vertebral body access instruments, such as trocars, access needles and working cannulas. In the illustrated embodiment, cannula 104 accesses the interior region of vertebral body 70 through access cannula 133. In alternative embodiments, an access cannula is not used and cannula 104 is inserted through the transpedicular access port. Depending on the particular procedure, cannula 104 can access the vertebral body through other approaches as well, such as from lateral or anterior approaches.

Figure 12B:
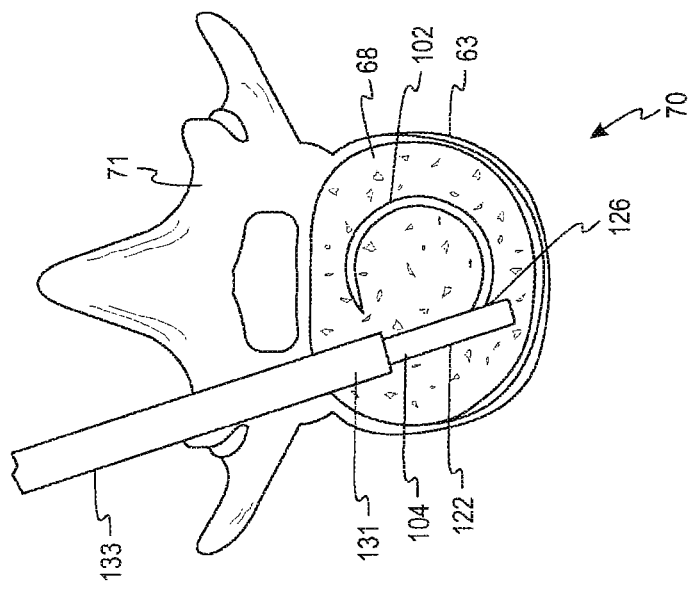
FIGS. 12a-12d are top cross-sectional views of a vertebra with the channeling device in various positions.
Figure 12A:
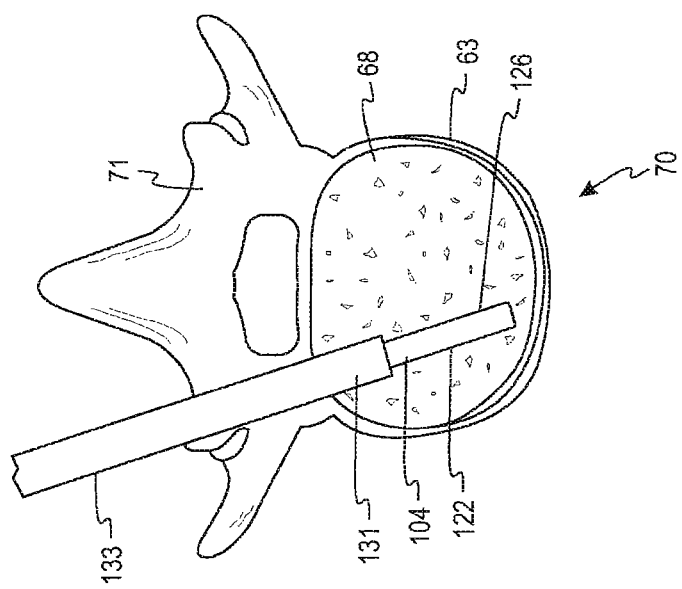

Referring to FIG. 12a, distal end portion 122 of the cannula 104 is inserted through access cannula 133 until it is in the desired position within vertebral body 70. In the illustrated embodiment, cannula 104 is centrally positioned within the vertebral body 70. However, the cannula may be positioned at other locations and orientations within vertebral body 70 depending on the desired application. Once cannula 104 is in the desired position within the vertebral body 70, elongated member 102, in its constrained or generally linear configuration, is advanced through cannula 104 and out of opening 126 in distal end portion 122 of cannula 104, as shown in FIG. 12b.

Upon exiting cannula 104 and traversing through bone structure, the external force provided by cannula 104 and constraining elongated member 102 in the generally linear configuration is removed and the elongated member, due to its shape retention or memory characteristics, begins to substantially revert or self-form into its initial or original arcuate shape. Thus, the deployed configuration of elongated member 102 is substantially the same as its initial or original configuration.

As elongated member 102 advances out of the distal end portion 122 of cannula 104, elongated member 102, due to its mechanical strength and shape retention characteristics, penetrates and transverses through the relatively spongy cancellous bone along an arcuate shaped path.

Channeling device 100 allows for incremental deployment and directional control of elongated member 102. The user can selectively choose how much of the elongated member is deployed out of the distal end portion of the cannula and how far he/she would like to advance elongated member 102 into the bone structure. For example, a desired portion of the elongated member may be deployed from the cannula. The desired portion may, depending on the procedure, be between about 0.10 and a full loop of the elongated member or the desired portion may be multiple loops or windings of the elongated member. In example 0.5 of a loop is deployed from the cannula and into the bone structure. Additionally, the deployment of elongated member 102 can be monitored by fluoroscopic imaging or any other suitable type imaging to help ensure that the elongated member is traveling along the desired path for the particular procedure. Monitoring the deployment of the elongated member provides several benefits, such as, providing an indication that the elongated member is being deployed along the desired path and in the desired orientation.

Figure 12C:
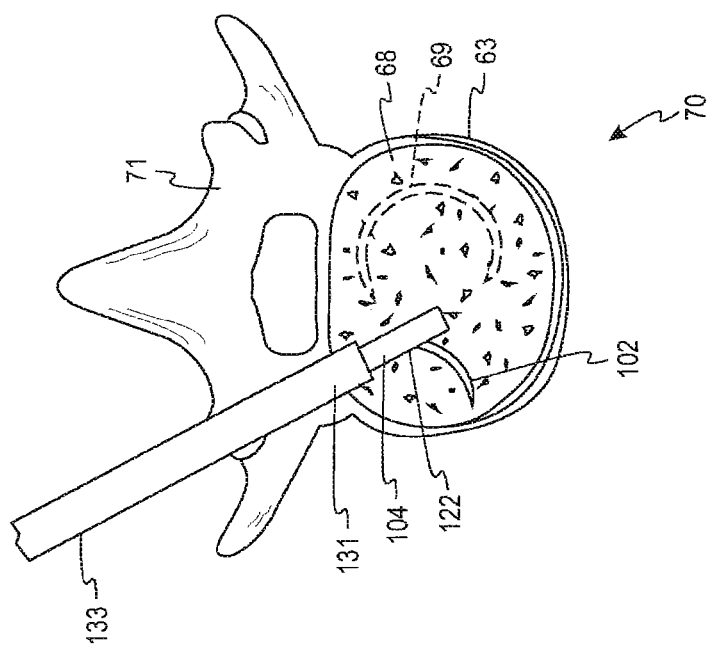

Turning to FIG. 12c, after the desired portion of elongated member 102 has been deployed and traversed through the internal region of the vertebral body, i.e., a sufficient length of the elongated member has been deployed to create a channel of the desired size, elongated member 102 is retracted from cancellous bone 68 of vertebral body 70 and back into cannula 104, thereby leaving a channel 69 within cancellous bone 68. As elongated member 102 is retracted into the cannula 104, the cannula again applies an external force on the elongated member and the elongated member is forced into its generally linear modified or pre-deployment configuration.

Figure 12D:
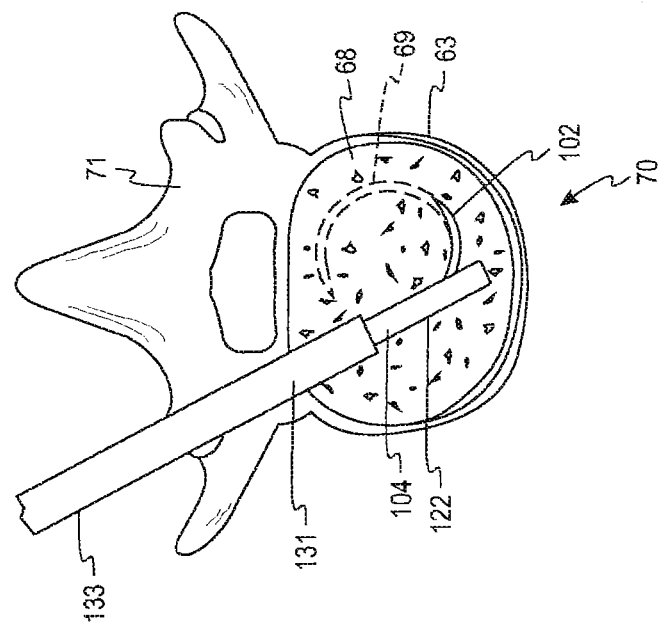

Referring to FIG. 12d, the user can reposition cannula 104 and then redeploy or advance elongated member 102 back through the bone structure along a second path in order to form an additional channel within the vertebral body. This process may be repeated to form a plurality of channels within the cancellous bone. After each deployment and retraction of elongated 102, cannula 104 may be repositioned or relocated within vertebral body 70. For example, cannula 104 may be rotated such that opening 126 is orientated in a different direction from the previous deployment of elongated member 104. Cannula 104 may be rotated any amount, for example, 30, 60, 90, 120, 150 or 180 degrees relative the location of the previous deployment. In one embodiment, cannula 104 may be positioned such that when the elongated member 102 is re-deployed out of cannula 104, it forms a channel that does not completely coincide with another channel. In addition, cannula 104 can be repositioned by axially advancing or retracting cannula 104 within the bone tissue or by repositioning the distal end portion 122 of cannula 104 up, down, and/or side to side. It will be understood that any combination of repositioning movements also may be by used to reposition cannula 104, e.g., rotating cannula 104, moving it axially and to one side. This method allows the user to form numerous permutations of channel configurations within bone tissue.

Figure 12E:
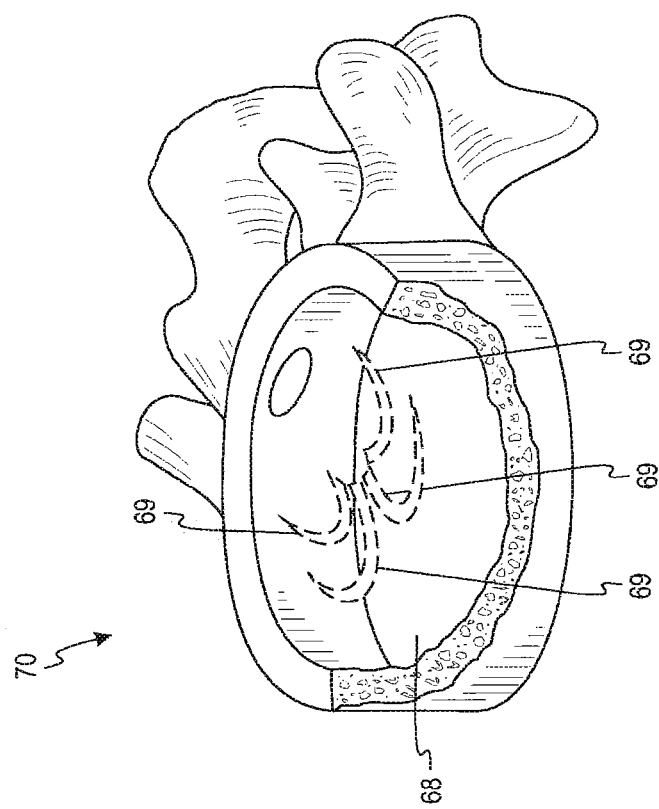
FIG. 12e is a perspective view of the vertebral body of FIGS. 12a-12d showing various channels created by the channeling device.

Referring to FIG. 12e, after the desired number and orientation of channels 69 have been created within cancellous bone and elongated member 102 has been fully or substantially retracted into cannula 104, elongated member 102 and deployment cannula 104 are withdrawn from the bone tissue, thereby leaving channels 69 within the bone structure.

After the channel or channels 69 have been created in the bone structure, i.e. cancellous bone, it may be desirable to fill the channels with a bone filler material, for example, bone cement, autograph, allograph, drugs, therapeutic agents, or osteoconductive materials that promote bone growth. If the bone filler is a curable material, such a curable bone cement, after the bone filler material has cured, it is contemplated that it will aid in stabilizing and supporting the cancellous bone and surrounding cortical bone, thereby reducing the risk of collapse or fracture while maintaining the original cancellous bone intact and avoiding the compaction of the bone and creation of a cavity as required in Kyphoplasty.

In one embodiment, after the channeling process is complete, channeling device 100 is removed from the bone tissue and a separate bone filler delivery device or member is positioned within the tissue site. The delivery device may include a bone filler delivery conduit 121 that may be inserted through the same access port 123 as the channeling device and may be inserted through the access cannula 133 (FIG. 12a) when one is present. Alternatively, the bone filler delivery conduit can be inserted through a second or different access port, such as a lateral or anterior access port. Moreover, the positioning of the delivery device can be monitored using fluoroscopy to ensure proper positioning of the needle. Distal end portion 125 of conduit 121 may be positioned to deliver bone filler material directly into a channel 69 such that bone filler material is directly injected or substantially directed into the channel. Alternatively, conduit 121 may be designed and positioned to inject or delivery bone filler material into the general area of channel or channels 69 wherein the bone filler material seeps and/or naturally flows into channels 69.

The delivery conduit 121 generally includes a cannula having at least one opening 127 through which the bone filler material can be delivered. As illustrated in FIG. 12F, Opening 127 can be generally aligned with at least one of the channels 69 in the bone tissue for delivering bone filler directly into the channel. Once the bone filler delivery device in the desired position, bone filler material 79 may be injected into the channel or channels 69. In one embodiment, as the bone filler material 79 progresses through the channel(s) 69, the bone filler material may be such that it interdigitates with the spongy or porous cancellous bone tissue. In other words, the bone filler material migrates or seeps into and through the pores and around the trabeculae of the spongy cancellous bone. A variety of factors contribute to amount of interdigitation and such factors can be controlled by a surgeon to achieve a desired result. Such factors can include, but are not limited to, the size of the channel created in the bone tissue, the viscosity and volume of bone filler material injected, the curing rate of the bone filler material and the amount of injection pressure applied during injection of the bone filler material.

Figure 12G:
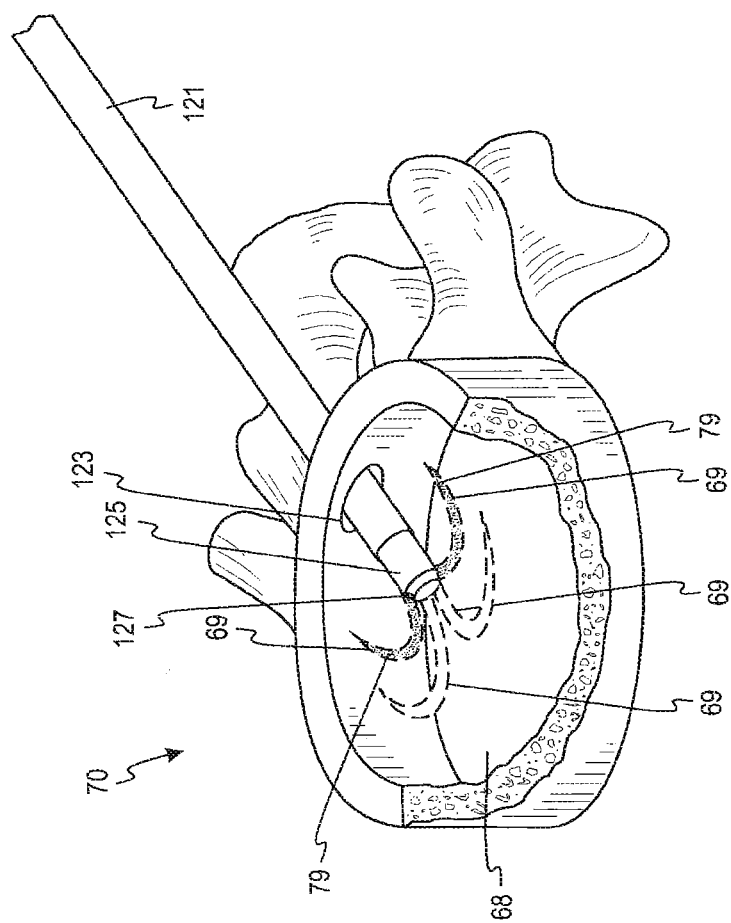
FIG. 12g is a perspective view of the vertebral body of FIG. 12e shown with bone filler being delivered into a second channel.

After bone filler is delivered into a channel 69, conduit 121 may be repositioned to deliver bone filler directly into another channel 69, e.g. opening 127 may be generally aligned with another channel 69, as illustrated in FIG. 12g.

In an alternate embodiment, it may be preferable to deliver the bone filling material during the channel creation process or immediately thereafter without removal of the channeling device. In these embodiments, bone filler delivery is incorporated into the channeling device and more specifically the elongated member.

In one embodiment, the elongated member is hollow and has an interior lumen, passageway or pathway that is sufficiently to allow the flow of the bone filler material along the elongated member. The bone filler material may be introduced into the interior lumen of the elongated member through an injection port located within the cannula or in the housing of the device. A flexible coupling and/or seals at the proximal end of the cannula may be employed to ensure the forward flow of material. Thus, immediately after a channel is created, the bone filler material may be injected by the user in a controlled manner. In one embodiment, the bone filler material may be injected to fill or "back-fill" the channel as the elongated member is being withdrawn from the channel and back into the cannula.

Figure 13B:
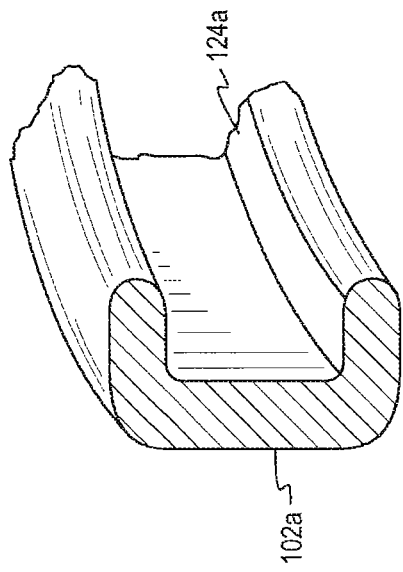
FIG. 13b is a partial cross-sectional view of the elongated member of 13a taken along lines 13b-13b.
Figure 13A:
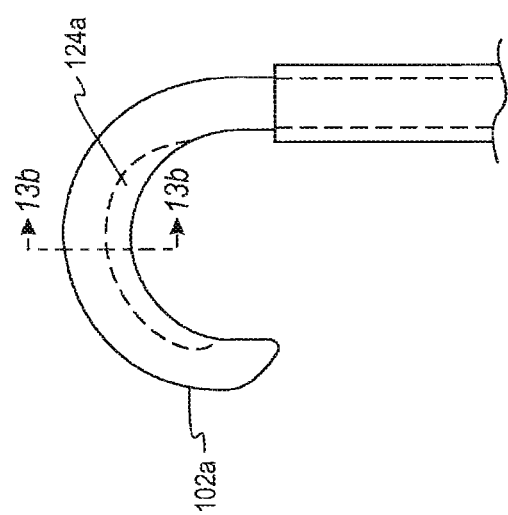
FIG. 13a is a plan view of one embodiment of a bone channeling device with an elongated member that has a passageway for delivering bone filler.

In an alternate embodiment illustrated in FIG. 13a, elongated member 102a has a "C" shaped cross-section that forms a passageway, pathway or groove 124a. The interior of the "C" faces toward the center of the loop defined by elongated member 102a. The pathway 124a may or may not extend all the way to the tip of elongated member 102a.

In use, after elongated member 102a has been deployed within bone structure, such as cancellous bone, bone filler material is injected along pathway 124a of elongated member 102a. The bone filler material may be injected along pathway 124a simultaneously or immediately after the channel in the bone structure is created.

IV. Bone Filler Delivery Members

As mentioned above, a separate device may be used in order to deliver bone filler material to channel(s) formed by the channeling device. Bone filler delivery devices or members include a source of bone filler operably connected to a bone filler conduit. The bone filler delivery conduit is inserted into bone structure and bone filler travels from the source along the conduit and into the bone structure. Various embodiments of bone filler delivery conduits are described below. The bone filler delivery devices disclosed herein may be part of a kit or system that includes any of the bone channel devices disclosed herein.

In one embodiment, the bone filler may be delivered in a generally radial direction, which may be useful in directing bone filler material into the channel formed by the elongated member. However, there are also instances in which the user may want to direct bone filler flow generally axially. For instance, when the procedure is nearly complete and all instruments are being withdrawn from the tissue site, the user may desire to fill the axial remaining space, for example, the space left by the former presence of the channeling device's cannula.

One embodiment of a conduit that may be used with a bone filler delivery device to direct bone filler material into channels created by a channeling device is illustrated in FIG. 14. Cannula 200 includes a curved distal end portion 203 and a distal end opening 202. Cannula 200 also includes a proximal end portion (not shown) which may be connected to a bone filler material source (not shown).

The design of cannula 200 is somewhat similar to what is known as an epidural or Touhy needle. Similar to a Touhy needle, opening 202 is not located in a sidewall of the cannula, but is instead located at the distal tip of the cannula. Distal end portion 203 is curved in such a way that distal end opening 202 is generally non-axial with the longitudinal axis of the cannula and opens in a radial direction. Bone filler material exiting the cannula is delivery in a generally radial direction or has a generally radial component. In use, opening 202 can be generally aligned with the channel(s) created by any of the above-mentioned bone channeling devices so that bone filler is delivered directly into the channel.

FIGS. 15-18 illustrate another embodiment of a bone filler material delivery conduit 200a. Delivery conduit 200a includes two concentric members (see, FIGS. 17 and 18), more specifically, an inner cannula 202a (FIG. 15) positioned within an outer cannula 204a (FIG. 16). As depicted in FIG. 15, inner cannula 202a has an opening 206a defined in the distal end portion 205a of the inner cannula. Opening 206a is in both end wall 207a and sidewall 209a of inner cannula 202a. Referring to FIG. 16, outer cannula 204a includes a distal end portion 211a including a first opening 208a defined in sidewall 213a of outer cannula 204a and a second opening 210a defined in an end wall 215a of outer cannula 204a. In the illustrated embodiment, second opening 210a has a semicircular shape, but could be other shapes as well.

Delivery conduit 200a allows for selective delivery of bone filler along two distinct flow paths. In the first configuration bone filler material is delivered in a direction substantially radially or has a radial component. As shown in FIG. 17, in the first configuration opening 206a of the inner cannula 202a is aligned with first opening 208a in the sidewall 213a of outer cannula 204a. When in the first configuration, bone filler material travels through inner cannula 202a and out of openings 206a and 208a in a radial direction. Turning now to FIG. 18, when in the second configuration, bone filler is directed substantially along the longitudinal axis of outer cannula 204a. In particular, the sidewall 209a of inner cannula 202a substantially obstructs flow through or substantially blocks off side opening 208a and bone filler ejected from opening 206a of inner cannula 202a is directed out of opening 210a of outer cannula 204a. In order to move from the first configuration to the second configuration and vice versa, the inner cannula 202a is rotated relative to outer cannula. In the illustrated embodiment inner cannula 202a is rotated about 180-degrees relative to the outer cannula 204a.

Figure 19:
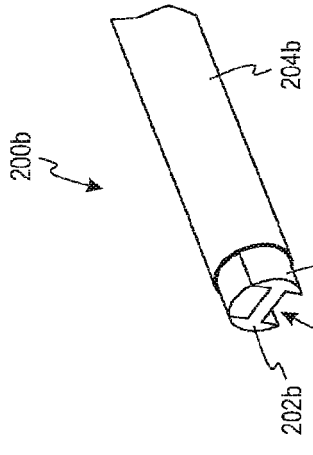
FIG. 19 is a perspective view of yet another embodiment of a bone filler delivery conduit shown in a first configuration.
Figures 20A, 20B:
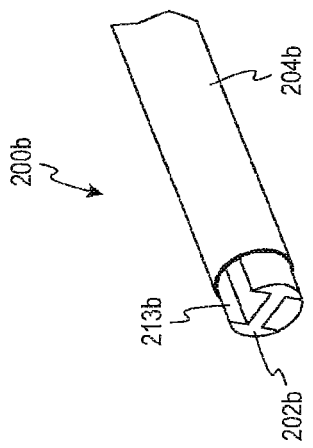
FIG. 20a is a perspective view of the bone filler delivery conduit of FIG. 19 shown in a second configuration.
FIG. 20b is another perspective view of the bone filler delivery conduit of FIG. 20a shown from the other direction.

Yet another embodiment of a bone filler material delivery conduit 200b for use with a bone filler delivery device is illustrated in FIGS. 19, 20a and 20b. Conduit 200b may be used for directional and selective delivery of bone filler along two distinct flow paths. Conduit 200b includes an inner cannula 202b movably positioned concentrically within an outer cannula 204b. Inner cannula 202b may have at least one, but preferably two longitudinal bone filler delivery passageways 212b and 213b. As illustrated in FIG. 19, passageway 212b is closed at the distal end 211b of inner cannula 202b and passageway 213b is opened at the distal end of inner cannula 202b.

In the first configuration bone filler material is delivered in the direction generally radially relative to the longitudinal axis of outer cannula 204b. Referring to FIG. 19, inner cannula 202b is positioned such that portions of both passageways 212b and 213b are exposed beyond the outer cannula 204b. Bone filler is then selectively driven down closed-ended passageway 212b and exits 212b in a generally radially direction or with a radial component.

In the second configuration, bone filler is directed substantially along the axis of the device. Referring now to FIGS. 20a and 20b inner cannula 202b is retracted such that closed end passageway 212b is fully within outer cannula 204b and substantially blocked off and passageway 213b is still exposed or open. When cannula 202b is partially extending from out cannula 204b, flow of bone filer material out of 213b may be in both a generally axial and radially direction. Alternatively, flow of bone filler material may be directed substantially generally axial by retracting inner cannula 202b fully into outer cannula 204b such that only the passageway 213b is exposed.

The switching mechanism for engaging either the first or the second passageway may be achieved in a variety of ways, but some preferable methods include using a switching valve or rotating the inner cannula with respect to a proximal port to which the source of bone filler is attached.

Figure 21:
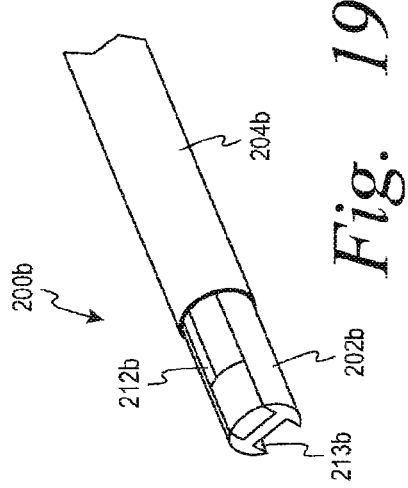
FIG. 21 is a perspective view of still yet another embodiment of a bone filler delivery conduit shown in a first configuration.
Figure 22:
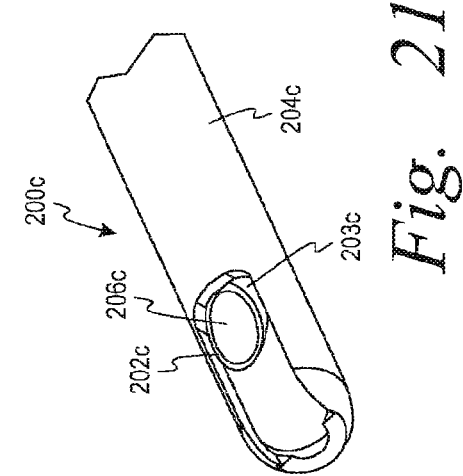
FIG. 22 is a perspective view of the bone filler delivery conduit of FIG. 21 shown in a second configuration.

Another embodiment of a bone filler delivery conduit is shown in FIGS. 21 and 22. In this embodiment, delivery conduit 200c includes an outer cannula 204c and inner cannula 202c. Inner cannula 202c may be similar to cannula 200 of FIG. 14 and is constructed of a material that allows the curved tip 203c of cannula 202c to deflect between a curved configuration and a straight configuration. Such materials may include shape memory metals, such Nitinol, or elastic polymers.

Referring to FIG. 21, when the bone filler delivery conduit is in the first configuration, opening 206c of inner cannula 202c is orientated in a generally radial direction, i.e., opening 206c faces radially outward away from the longitudinal axis of outer cannula 204c. Bone filler deployed along inner cannula 202c and exiting out of opening 206c is directed in a substantially radial direction and has a radial component. In the second configuration illustrated in FIG. 22, distal end portion 203c of inner cannula 202c is retracted into outer cannula 204c. When inner cannula 202c is retracted into outer cannula 204c, outer cannula 204c deflects distal end portion 203c of inner cannula 202c into a more linear configuration so that bone filler exiting out opening 206c of inner cannula 202c and opening 208c of outer cannula 204c in a substantially axial direction or having an axial component.

FIGS. 23 and 24 illustrate yet a further embodiment of a bone filler delivery conduit 200e that can provide delivery of bone filler in both a substantially axial direction and substantially radial direction. The conduit 200e includes an inner cannula 202e movably positioned within an outer cannula 204e. The cannulas translate axially relative to one another and may also be rotatable with respect to each other. As depicted in FIG. 24, the inner cannula 202e has one or more openings 214e defined in the distal end wall 224e of inner cannula 202e and also includes an opening 216e defined in the sidewall. Outer cannula 204e has an opening 218e defined in a distal end wall 222e and also includes an opening 220e defined in the sidewall of outer cannula 204e. It will be appreciated that the arrangement of the openings in the distal ends of the inner and outer cannulas may be in any variety of patterns.

There are two configurations for injecting cement from cement delivery conduit 200e. In the first configuration, opening 216e in the side wall of the inner cannula 202e and opening 220e in the outer cannula 204e align with one another and the outer surface of the distal end of inner cannula 202e mates or contacts with the inner surface of distal wall 222e of outer cannula 204e. This configuration prevents axial flow of bone filler out of opening 218e of outer cannula 204e because opening 218e is substantially blocked off by inner cannula 202e and openings 214e are substantially block off by outer cannula 204e. This configuration facilitates injection of bone filler in a generally radial direction through aligned openings 216e and 220e of the inner and outer cannulas, respectively.

When the device is in the second configuration, the inner cannula 202e is translated proximally relative to the outer cannula 204e, allowing communication between the openings 214e in the distal end of inner cannulas 202e and opening 218e of outer cannula 204e. At the same time, opening 216e of inner cannula 202e and 220e of outer cannula 204e are misaligned, therefore substantially blocking off openings 216e and 220e. In this configuration, the flow path of the bone filler is substantially along the axis of the device or has an axial component.

Another alternate embodiment of a bone filler delivery conduit 200f is illustrated in FIG. 25. Conduit 200f includes an inner cannula 202f located within an outer cannula 204f. Inner cannula 202f is sized such that there is a gap or pathway 203f between outer wall 206f of inner cannula 202f and inner wall 208f of outer cannula 204f. Inner cannula 202f has an opening 210f that is aligned with opening 212f of outer cannula 204f. In the illustrated embodiment, inner cannula 202f is similar to cannula 200 of FIG. 14.

When it is desired to direct bone filler in a radial direction, bone filler material is directed along inner cannula 202c and out of opening 210f. When it is desired to direct bone filler in a generally axial direction bone filler is directed through cannula 204f, along pathway 203f and out of an opening 212f in a substantially axial direction.

It will be understood that the embodiments of the present disclosure which have been described are illustrative of some of the applications of the principles of the present invention. Numerous modifications may be made by those skilled in the art without departing from the true spirit and scope of the invention, including those combinations of features that are individually disclosed or claimed herein.

What is claimed is:

1. A device for creating channels within bone tissue, comprising:
 a housing;
 a cannula size for insertion into bone tissue, the cannula extending from the housing and including a proximal end portion and a distal end portion, the proximal end portion of the cannula being rotatably connected to the housing such that the cannula and the housing are longitudinally fixed and rotatable relative to one another; and
 a generally elongated member for creating channels within bone tissue, the generally elongated member positioned within the cannula and having a first generally linear configuration for movement through the cannula, the elongated member having a portion that is selectively advanceable out of an opening in the distal end portion of the cannula and through bone tissue, wherein when the portion is advanced out of the opening the portion has a second generally non-linear configuration, and the portion being retractable into the opening in the distal end portion of the cannula, leaving a channel within bone tissue.

2. The device of claim 1 in which the second generally non-linear configuration comprises an arcuate configuration.

3. The device of claim 1 in which the second generally non-linear configuration comprises a helical configuration.

4. The device of claim 1 in which the second generally non-linear configuration comprises a looped configuration.

5. The device of claim 1 in which the second generally non-linear configuration comprises a spiral configuration.

6. The device of claim 1 in which the elongate member is comprised of a shape memory material.

7. The device of claim 1 in which the elongated member includes a distal tip that is configured to pierce bone tissue.

8. The device of claim 1 further including a drive mechanism for moving the elongated member within the cannula so as to selectively advance and retract the portion of the elongated member out of and into the opening in the distal end portion of the cannula.

9. The device of claim 8 in which a proximal end portion of the elongated member is rotatably connected to the drive mechanism, and the elongated member rotates relative to the drive mechanism when the housing and cannula are rotated relative to one another.

10. The device of claim 1 in which a hub rotatably connects a proximal end of the cannula with the housing.

11. The device of claim 1 in which a proximal end of the elongated member is configured to twist when the housing is rotated relative to the cannula.

12. The device of claim 11 in which the proximal end of the elongated member has a desired amount of torsional resistance which prevents relative rotation between the housing and the cannula until a sufficient force is applied to overcome the torsional resistance.

13. The device of claim 1 in which a desired amount of rotational resistance prevents relative rotation between the cannula and housing until a sufficient force is applied to overcome the rotational resistance.

14. The device of claim 1 in which the housing rotates while the cannula remains substantially stationary.

15. The device of claim 1 in which the elongated member includes a passageway for delivering bone filler material.

16. The device of claim 15 in which the elongated member includes a C-shaped cross-section that forms the passageway.

17. The device of claim 1 further including a bone filler material delivery device for delivering bone filler material into the channel within bone.

18. A system for creating channels within bone tissue and delivering bone filler within bone tissue, comprising:
 a housing;
 a cannula size for insertion into bone tissue, the cannula being connected to and extending from the housing such that the cannula and housing are longitudinally fixed relative to one another, the cannula including a proximal end portion and a distal end portion;
 a generally elongated member for creating channels within bone tissue, the generally elongated member positioned within the cannula and having a first generally linear configuration for movement through the cannula, the elongated member having a portion that is selectively advanceable out of an opening in the distal end portion of the cannula and through bone tissue, wherein when the portion is advanced out of the opening the portion has a second generally non-linear configuration, and the portion being retractable into the opening in the distal end portion of the cannula, leaving a channel within bone tissue; and
 a bone filler material delivery member for delivering bone filler material into the channel, wherein the bone filler material delivery member selectively delivers bone filler material in a generally axial and a general radial direction.

19. The system of claim 18 wherein the proximal end portion of the cannula is rotatably connected to the housing such that the cannula and the housing are rotatable relative to one another.

20. The system of claim 18 in which a proximal end of the elongated member is configured to twist when the housing and cannula are rotated relative to one another.

21. The device of claim 18 in which the proximal end of the elongated member has a desired amount of torsional resistance which prevents relative rotation between the housing and the cannula until a sufficient force is applied to overcome the torsional resistance.

22. The system of claim 18 in which a desired amount of rotational resistance prevents relative rotation between the cannula and housing until a sufficient force is applied to overcome the rotational resistance.

23. The system of claim 18 in which the housing rotates while the cannula remains substantially stationary.

24. The system of claim 18 in which the bone filler material delivery member delivers bone filler material substantially directly into the channel within the bone.

25. The system of claim 18 in which the second generally non-linear configuration comprises an arcuate configuration.

26. The system of claim 18 in which the second generally non-linear configuration comprises a looped configuration.

27. The system of claim 18 in which the second generally non-linear configuration comprises a helical configuration.

28. The system of claim 18 further including a drive mechanism for moving the elongated member within the cannula so as to selectively advance and retract the portion of the elongated member out of and into the opening in the distal end portion of the cannula.

29. The system of claim 18 in which a hub connects the proximal end of the cannula with the housing.

30. The system of claim 18 in which the elongate member is comprised of a shape memory material.

31. The system of claim 18 in which the elongated member includes a distal tip that is configured to pierce bone tissue.

32. A device for creating channels within bone tissue, comprising:
   a housing;
   a cannula size for insertion into bone tissue, the cannula extending from the housing and including a proximal end portion and a distal end portion, the proximal end portion of the cannula being rotatably connected to the housing, wherein in an amount of rotational resistance prevents relative rotation between the cannula and housing until a sufficient force is applied to overcome said resistance; and
   a generally elongated member for creating channels within bone tissue, the generally elongated member positioned within the cannula and having a first generally linear configuration for movement through the cannula, the elongated member having a portion that is selectively advanceable out of an opening in the distal end portion of the cannula and through bone tissue, wherein when the portion is advanced out of the opening the portion has a second generally non-linear configuration, and the portion being retractable into the opening in the distal end portion of the cannula, leaving a channel within bone tissue.

33. The device of claim 32 in which the second generally non-linear configuration comprises an arcuate configuration.

34. The device of claim 32 in which the second generally non-linear configuration comprises a helical configuration.

35. The device of claim 32 in which the second generally non-linear configuration comprises a looped configuration.

36. The device of claim 32 in which the second generally non-linear configuration comprises a spiral configuration.

37. The device of claim 32 in which the elongate member is comprised of a shape memory material.

38. The device of claim 32 in which a proximal end of the elongated member is configured to twist when the housing is rotated relative to the cannula.

39. The device of claim 38 in which the proximal end of the elongated member has a desired amount of torsional resistance which provides the rotational resistance that prevents rotation between the housing and the cannula until the force applied is sufficient to overcome the torsional resistance.

40. The device of claim 32 in which the elongated member includes a passageway for delivering bone filler material.

* * * * *